US011198711B2

(12) United States Patent
Fitches et al.

(10) Patent No.: US 11,198,711 B2
(45) Date of Patent: Dec. 14, 2021

(54) PESTICIDAL FUSION PROTEIN IMPROVEMENTS

(71) Applicants: University of Durham, Durham (GB); The Secretary of State for Environment, Food and Rural Affairs, Yorkshire (GB)

(72) Inventors: Elaine Charlotte Fitches, Middlesbrough (GB); John Arthur Gatehouse, Stanley (GB); Prashant Shivasharan Pyati, Durham (GB); Sheng Yang, Durham (GB)

(73) Assignee: University of Durham, Durham (GB)

( * ) Notice: Subject to any disclaimer, the term of this patent is extended or adjusted under 35 U.S.C. 154(b) by 0 days.

(21) Appl. No.: 16/123,860

(22) Filed: Sep. 6, 2018

(65) Prior Publication Data

US 2019/0119336 A1 Apr. 25, 2019

Related U.S. Application Data

(63) Continuation of application No. 15/103,810, filed as application No. PCT/GB2014/053663 on Dec. 11, 2014, now abandoned.

(30) Foreign Application Priority Data

Dec. 11, 2013 (GB) ..................................... 1321938

(51) Int. Cl.
*C07K 14/435* (2006.01)
*C07K 14/42* (2006.01)
*A01N 37/46* (2006.01)

(52) U.S. Cl.
CPC ........ *C07K 14/43518* (2013.01); *A01N 37/46* (2013.01); *C07K 14/42* (2013.01); *C07K 2319/02* (2013.01); *C07K 2319/35* (2013.01); *C07K 2319/55* (2013.01)

(58) Field of Classification Search
CPC ........ C07K 14/43513; C07K 14/43504; C07K 2319/00; C07K 2319/02; C07K 2319/55
See application file for complete search history.

(56) References Cited

U.S. PATENT DOCUMENTS

| | | | | |
|---|---|---|---|---|
| 5,763,568 | A | 6/1998 | Atkinson et al. | |
| 7,196,057 | B2 | 3/2007 | Gatehouse et al. | |
| 7,354,993 | B2 | 4/2008 | King et al. | |
| 7,575,758 | B2 * | 8/2009 | King | C07K 14/43518 424/405 |
| 7,951,929 | B2 * | 5/2011 | King | A01N 37/46 536/23.5 |
| 2004/0138423 | A1 | 7/2004 | King et al. | |
| 2007/0066529 | A1 | 3/2007 | King et al. | |
| 2014/0366227 | A1 | 12/2014 | Gatehouse et al. | |
| 2016/0311867 | A1 | 10/2016 | Fitches et al. | |

FOREIGN PATENT DOCUMENTS

| | | | | |
|---|---|---|---|---|
| WO | WO9958705 A1 | 11/1999 | | |
| WO | WO2003014150 A2 | 2/2003 | | |
| WO | WO2005025312 A2 | 3/2005 | | |
| WO | WO2006052806 A2 | 5/2006 | | |
| WO | 2007035382 A2 | 3/2007 | | |
| WO | WO-2012131302 A1 * | 10/2012 | | A01N 43/50 |
| WO | WO2012131302 A1 | 10/2012 | | |
| WO | WO2013026105 A1 | 2/2013 | | |

OTHER PUBLICATIONS

Tedford et al., "Australian funnel-web spiders: master insecticide chemists", Toxicon, 2004, pp. 601-618 (Year: 2004).*
Windley et al. "Spider-Venom Peptides as Bioinsecticides", Toxins, 2012, pp. 191-227 (Year: 2012).*
Fitches et al. Fusion to Snowdrop Lectin Magnifies the Oral Activity of Insecticidal w-Hexatoxin-Hv1a Peptide by Enabling Its Delivery to the Central Nervous System:, PLOS One, Jun. 2012, 1-10 (Year: 2012).*
Back, E.J., Dec. 8, 2011, Insecticidal Fusion Proteins for the control of coleopteran pests, Durham e-Theses, http://e-theses.dur.ac.uk/3283/.
Bloomquist, "Mode of action of atracotoxin at central and peripheral synapses of insects," article (2003) pp. 45-50.
Bonning et al., "Toxin delivery by the coat protein of an aphid-vectored plant virus provides plant resistance to aphids", Nature Biotechnology, vol. 32, No. 1, Jan. 2014 (pp. 102-106).
Brown et al., "Differentially Regulated Inhibitor-Sensitive and Insensitive Protease Genes from the Phytophagous Insect Pest, Helicoverpa armigera, are Members of Complex Multigene Families," article (1997) vol. 27, No. 7, pp. 625-638.
Catterall, "Structure and Regulation of Voltage-Gated Ca2+ Channels," article (2000) pp. 521-555.
Chong et al., "The omega-atracotoxins: Selective blockers of insect M-LVA and HVA calcium channels," Biochemical Pharmacology, vol. 74, No. 4, (2007), pp. 623-638.
Cino, "High Yield Protein Production from Pichia pastoris Yeast: A Protocol for Benchtop Fermentation," article (May 1999) pp. 1-12.
Cregg et al., "Recent Advances in the Expression of Foreign Genes in Pichia pastoris," article (1993) vol. 11, pp. 905-910.
Douglas et al., "Synthesis of the Essential Amino Acid Tryptophan in the Pea Aphid (Acyrthosiphon Pisum) Symbiosis," article (1992) vol. 38, No. 8, pp. 565-568.
Down et al., "Insecticidal spider venom toxin fused to snowdrop lectin is toxic to the peach-potato aphid, Myzus persicae (Hemiptera:Aphididae) and the rice brown planthopper, Nilaparvata lugens (Hemiptera:Delphacidae)," Pest Management Science, vol. 62, No. 1, Jan. 2006, pp. 77-85.
European Search Report completed for European Application No. GB1105418.6, dated Feb. 15, 2012.
Fitches et al. "New environmentally-friendly technologies for slug control based on orally-delivered fusion proteins containing specific molluscicidal toxins," Novara (May 2012) 86 pages, URL:http://randd.defra.gov.uk/Document.aspx?Document=12094_FinalreportLK0991.pdf.

(Continued)

*Primary Examiner* — Lianko G Garyu
(74) *Attorney, Agent, or Firm* — Michael Best & Friedrich LLP

(57) ABSTRACT

Methods of increasing the biological activity of toxins. Methods of increasing the biological activity of pesticide toxins through the incorporation of pro-regions into nucleic acid constructs for the production of said toxins.

21 Claims, 12 Drawing Sheets

Figures 1A, 1B:
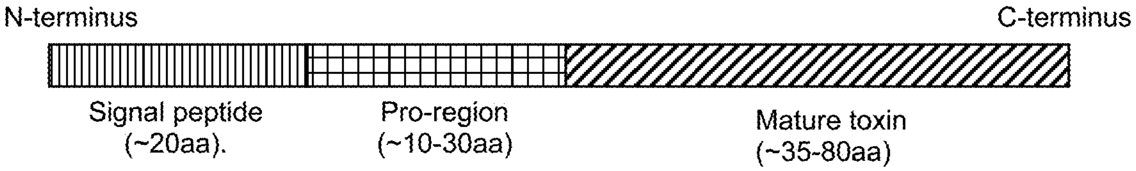

Specification includes a Sequence Listing.

(56) References Cited

OTHER PUBLICATIONS

Fitches et al., "An evaluation of garlic lectin as an alternative carrier domain for insecticidal fusion proteins," article 483 Sciences Insect Science (2008) 15, 483-495, DOI 10.1111/j.1744-7917.2008.00237.x, Journal compilation © Institute of Zoology, Chinese Academy of Sciences.
Fitches et al., "Fusion proteins containing insect-specific toxins as pest control agents: snowdrop lectin delivers fused insecticidal spider venom toxin to insect haemolymph following oral ingestion," Journal of Insect Physiology, 2004, 50: 61-71.
Fitches et al., "The insecticidal activity of recombinant garlic lectins towards aphids," article, Insect Biochemistry and Molecular Biology 38 (2008) 905-915, Elsevier Ltd.
Fitches, "Fusion to Snowdrop Lectin Magnifies the Oral Activity of Insecticidal 1 Hexatoxin Hvl a Peptide by Enabling Its Delivery to the Central Nervous System," p. 1 Jun. 11, 2012.
Fitches, "A comparison of the short and long term effects of insecticidal lectins on the activities of soluble and brush border enzymes of tomato moth larvae," article (1998) pp. 1213-1224.
Fletcher et al., "The Structure of a Novel Insecticidal Neurotoxin, w-atractoxin-HV1, from the venom of an Australian funnel web spider," article (1997) vol. 4, No. 7, pp. 559-566.
Gordon et al., "The differential preference of scorpion x-toxins for insect or mammalian sodium channels: Implications for improved insect control," article (2006) pp. 452-472.
Hogervorst et al., "Direct effects of snowdrop lectin (GNA) on larvae of three aphid predators and fate of GNA after ingestion," Journal of Insect Physiology 52: 614-624, 2006.
Khan et al., "Spider venom toxin protects plants from insect attack," Transgenic Research, Kluwer Academic Publishers—Plenum Publishers, NE, vol. 15, No. 3, Jun. 1, 2006.
Khan et al., "Spider Venom Toxin Protects Plants from Insect Attack," article (2006) pp. 349-357.
Kalapothakis et al., "Cloning of cDNAs Encoding Neurotoxic Peptides from the Spider Phoneutria Nigriventer," Toxicon (1998) pp. 1843-1850.
Kozlov et al., "A Novel Strategy for the Identification of Toxinlike Structures in Spider Venom," Proteins: Structure, Function, and Bioinformatics, vol. 59, No. 1, (2005), pp. 131-140.
Laurino et al., "Toxicity of Neonicotinoid Insecticides to Honey Bees: Laboratory Tests," article (2011) pp. 107-113.
Liao et al., "Solution Structure and Functional Characterization of Jingzhaotosin-XI:Novel Gating Modifier of both Potassium and Sodium Channels," Biochemistry (2006) 15591-15600.
Mukherjee et al., "Orally Active Acaricidal Peptide Toxins from Spider Venom," article (2006) pp. 182-187.
OECD/OCDE, "OECD Guidelines for the Testing of Chemicals—Honeybees, Acute Oral Toxicity Test—Document 213," article (1998) pp. 1-8.
OECD/OCDE, "OECD Guidelines for the Testing of Chemicals—Honeybees, Acute Oral Toxicity Test—Document 214" article (1998) pp. 1-7.
Office Action from the US Patent and Trademark Office for U.S. Appl. No. 14/008,412 dated Oct. 7, 2016 (29 pages).
Office Action from the US Patent and Trademark Office for U.S. Appl. No. 15/103,810 dated May 17, 2017 (11 pages).
Office Action from the US Patent and Trademark Office for U.S. Appl. No. 15/103,810 dated Aug. 9, 2017 (18 pages).
PCT/GB2014/053663 International Search Report dated Sep. 3, 2015 (4 pages).
Peumans et al., "Lectins as Plant Defense Proteins," article, Plant Physiol. (1995) 109: 347-352, Laboratory for Phytopathology and Plant Protection, Katholieke Universiteit Leuven.
Pyati et al. "Optimising expression of the recombinant fusion protein biopesticide [omega]—hexatoxin-Hvla/GNA in Pichia pastoris: sequence modifications and a simple method for the generation of multi-copy strains", Journal of Industrial Microbiology & Biotechnology, vol. 41, No. 8, (2014), pp. 1237-1247.
Raemaekers et al., "Functional Phytohemagglutinin (PHA) and Galanthus nivalis agglutinin (GNA) expressed in Pichia Pastoris," article (1999) pp. 394-403.
Santos et al., "The A-superfamily of Conotoxins: Structural and Functional Divergence," article, The Journal of Biological Chemistry, 2004, p. 17596-17606.
Tedford et al., "Australian funnel-web spiders: master insecticide chemists," article, Toxicon 43 (2004) 601-618, Elsevier Ltd.
Tedford et al., "Functional Significance of the b-Hairpin in the Insecticidal Neurotoxin w-Atracotoxin-Hv1a," article (2001) vol. 276, No. 28, p. 26568-26576.
Tedford et al., "Scanning Mutagenesis of ω-Atracotoxin-Hv1 a Reveals a Spatially Restricted Epitope That Confers Selective Activity against Insect Calcium Channels," article (2004) p. 44133-44140.
Trung et al., "A fusion protein containing a lepidopteran-specific toxin from the South Indian red scorpion (Mesobuthus tamulus) and snowdrop lectin shows oral toxicity to target insects," BMC Biotechnology, Biomed Central Ltd., vol. 6, No. 1, Mar. 16, 2006.
Van Damme et al., "Accession ID M55556.1," public available Apr. 27, 1993.
Wang et al., "Structure-function studies of omega-atracotoxin, a potent antagonist of insect voltage-gated calcium channels," European Journal of Biochemistry, Blackwell Publishing, Berlin, DE, vol. 264, No. 2, Sep. 1, 1999.
Windley et al., "Spider-Venom Peptides as Bioinsecticides," article, Toxins, Mar. 2012, pp. 191-227.
Wong et al., "SVM-Based Prediction of Propeptide Cleavage Sites in Spider Toxins Identifies Toxin Innovation in an Australian Tarantula," PLOS One, vol. 8, No. 7, (2013) p. e66279.
G. Ferrat, et al., "Solution Structure of Two Insect-Specific Spider Toxins and Their Pharmacological Interaction With the Insect Voltage-Gated Na+ Channel", Proteins: Structure, Function, and Bioinformatics, 2005, vol. 59, pp. 368-379.
O. Buczek, et al., "Propeptide does not act as an intramolecular chaperone but facilitates protein disulfide isomerase-assisted folding of a conotoxin precursor", Biochemistry, 2004, vol. 43(4), pp. 1093-1101.
Examination Report issued from the Australian Patent Office for related Application No. 2014363158 dated Aug. 16, 2018, 6 Pages.
Office Action issued from the Japanese Patent Office for related Application No. 2016-558436 dated Oct. 23, 2018 12 Pages including English Translation.

* cited by examiner

EDTRADLQGGEAAEKVFRRSPTCIPSGQPCPYNENCCSQSCTFKENENGNTVKRCD (A)

(B)

(A) Pl1a injection (B) Injection Pl1a and Ao1bPro-Pl1a – Dose A = Pl1a; Dose B = Ao1bPro-Pl1a

PESTICIDAL FUSION PROTEIN IMPROVEMENTS

CROSS-REFERENCE TO RELATED APPLICATIONS

This application is a continuation of U.S. patent application Ser. No. 15/103,810, filed Jun. 10, 2016 now abandoned, which is a national stage filing under 35 U.S.C. 371 of International Patent Application No. PCT/GB2014/053663, filed Dec. 11, 2014 which claims priority to United Kingdom Patent Application No. 1321938.1, filed Dec. 11, 2013, the entire contents of all of which are hereby incorporated by reference herein.

SEQUENCE LISTING

The instant application contains a Sequence Listing which has been submitted electronically in ASCII format and is hereby incorporated by reference in its entirety. Said ASCII copy, created on Jun. 10, 2016 is named "063511-9229-US00-Sequence Listing—AS FILED" and is 19,659 bytes in size.

FIELD OF THE INVENTION

The present invention relates to methods of increasing the biological activity of recombinant toxins. The invention also relates to nucleic acid constructs containing a pro-region and the sequence of a toxin, in particular an arthropod toxin.

BACKGROUND OF THE INVENTION

Against a background of increasing global population, the pressures on food production systems to become more efficient are ever increasing. Pests are still a major constraint on crop production despite progress in crop protection measures. Estimates of the potential losses worldwide for the top six crops vary from 25-80% (40% for potato). Some pests and diseases can be controlled by the application of agrochemicals. However, despite the wide range of pesticides available on the market, plant disease is still a major concern.

In the past the majority of research on developing pesticides focused on the identification of chemical entities which could be used for this purpose. However, these non-target specific pesticides often result in environmental damage and can have a negative impact on non-target species (including animal species) and human health. As a result, European Union legislation has been approved which bans certain chemical compounds from use in pesticides. There has, therefore, been a shift to identifying new types of "biopesticides" that can be used for pest management. Biopesticides are generally considered as naturally occurring substances (biochemical pesticides), microorganisms capable of controlling pests (microbial pesticides) and pesticidal substances produced by plants containing added genetic material (plant-incorporated protectants). It is hoped that this drive towards developing biopesticides will result in more environmentally friendly options for preventing plant disease.

Neuropeptide toxins synthesised as venom by spiders and other arthropods have been the subject of research for development as biopesticides. WO2006/052806, WO2005/025313 and US2007/0066529 describe the use of spider toxin venom peptides for use as a biopesticide and Khan et al., 2006 described expression of spider venom toxin in plants to protect the plants from insect attack. The present inventors have previously shown that ω-ACTX-Hv1a, a toxin derived from the funnel-web spider *Hadroncyhe versuta*, when fused to a protein capable of mediating translocation of the fusion protein from the invertebrate gut, such as the snowdrop lectin "carrier" GNA, can function as an effective pesticide against a broad range of pests (WO2012/131302).

SUMMARY OF THE INVENTION

The present invention in based in part on studies by the inventors into the effect of inclusion of a pro-region in a construct for expression of a recombinant toxin on the biological activity of said recombinant toxin.

The present investigators wished to determine how the biological activity of recombinant toxin proteins expressed in vitro might be further improved. To investigate this, the present inventors analysed the DNA sequences of the genes encoding arthropod toxins. The arthropod toxins utilised in WO2012/131302 are small, cysteine-rich proteins belonging to several superfamilies of protein sequences (which include toxins from organisms other than arthropods). The encoding genes include two sequences that are not present in the final protein product; a predicted N-terminal signal peptide that is removed during translation and a predicted pro-region, between the signal peptide and the final sequence of the protein as isolated (see FIG. 1A). Pro-regions are a common feature of small peptide toxins in arthropods and other organisms (Windley et al., 2012). The present inventors have surprisingly found that the inclusion of this predicted pro-region in a construct for expression of a recombinant toxin results in greater biological activity compared to a toxin produced from a construct lacking a pro-region. Furthermore, inclusion of a pro-sequence in a construct for the expression of a toxin which does not naturally contain a pro-sequence in its genomic DNA sequence (for example δ-amaurobitoxin-PI1a) again results in an increased biological activity compared to a toxin produced from a construct lacking a pro-sequence.

Accordingly, in a first aspect of the invention, there is provided a method of increasing the biological activity of a recombinant toxin, the method comprising:

providing a nucleic acid construct comprising: (i) a toxin sequence, or a fragment or variant thereof, linked to (ii) a pro-region, or fragment or variant thereof; and optionally expressing the recombinant toxin.

In a second aspect of the invention, there is provided a nucleic acid construct comprising: (i) a pro-region, or fragment or variant thereof; and (ii) a site adjacent to the pro-region into which a toxin gene sequence, or fragment or variant thereof may be inserted.

In an embodiment in accordance with the second aspect of the invention, the nucleic acid construct further comprises the toxin gene sequence or fragment or variant thereof inserted into the site adjacent to the pro-region.

In a third aspect of the present invention there is provided a host cell comprising the nucleic acid construct according to the second aspect of the invention into which a toxin gene sequence has been inserted, or any embodiment thereof.

In a fourth aspect of the present invention there is provided a method of producing a recombinant toxin with increased biological activity, the method comprising culturing a host cell as defined in the third aspect of the invention under conditions suitable for expression of the recombinant toxin.

The toxin according to the abovementioned aspects of the invention is a pesticide toxin. In preferred embodiments of the invention, the toxin may be derived from arthropods, molluscs or other invertebrates.

In one embodiment of the invention, the toxin is an arthropod toxin. The arthropod toxins of the present invention may include ω-ACTX-Hv1a and κ-ACTX-Hv1c from *Hadronyche versuta*, δ-amaurobitoxin-PI1a from *Pireneitega luctuosus, Segestria florentina* toxins SfI1-8, *Buthus mesotamulus* toxin ButaIT, theraphotoxin Ec2a from *Eucratoscelus constrictus*, cyrtoautoxin Asia from *Apomastus schlingeri*, sicaritoxin Li1a from *Loxosceles intermedia*, and other similar toxins.

The toxin according to the present invention may comprise a peptide of 20-100 amino acid residues. The toxin may contain multiple cysteine residues forming internal disulphide bonds.

In one embodiment, the toxin is ω-ACTX-Hv1a, or a fragment or variant thereof. The ω-ACTX-Hv1a toxin is known in the art (Fletcher et al., 1997). It is a toxin isolated from the funnel-web spider *Hadroncyhe versuta*. The amino acid sequence of ω-ACTX-Hv1a is known, as is the nucleic acid sequence encoding ω-ACTX-Hv1a. ω-ACTX-Hv1a toxin is a calcium channel antagonist which has previously been shown to block invertebrate but not vertebrate calcium channels. In most circumstances it is desirable to use pesticides which do not have activity against vertebrate animals, so as to avoid deleterious effects on humans or animals.

It has previously been reported that ω-ACTX-Hv1a can be used on its own as a pesticide when applied topically to caterpillars (Khan et al., 2006). However, the authors of the abovementioned document report topical application of the peptide in a solution containing imidazole which is known to be insecticidal in its own right. Moreover, no further evidence for insecticidal activity of the peptide alone has been reported, with other disclosures covering ω-ACTX-Hv1a only stating activity by injections into invertebrate pest animals.

The present inventors have previously shown that the biological activity of recombinant ω-ACTX-Hv1a can be improved by creation of a fusion protein, whereby the toxin ω-ACTX-Hv1a is fused to a "carrier" peptide which can mediate translocation of the fusion protein from the invertebrate gut (WO2012/131302). The inventors used the plant lectin GNA as an example of such a carrier peptide.

To investigate how the biological activity of recombinant toxin fusion proteins might be otherwise improved, the present inventors analysed the DNA sequences of the genes encoding arthropod toxins, in particular ω-ACTX-Hv1a. It was found that many arthropod genes contain a predicted pro-region, not present in the final protein, which had not previously been incorporated into constructs for expressing fusion proteins in vitro. As can be seen herein, the inventors incorporated the sequence of the pro-region into a nucleic acid construct for the production of a recombinant toxin protein. The inventors found that a recombinant ω-ACTX-Hv1a produced from a construct containing a pro-region administered to a range of invertebrate pests either by injection or when included in the diet resulted in increased paralysis and mortality compared to producing the recombinant ω-ACTX-Hv1a from an unmodified construct (i.e. containing the ω-ACTX-Hv1a sequence without an additional pro-region). Therefore, ω-ACTX-Hv1a peptide toxin can be very effective as a pesticide to invertebrate animals when supplied in this form.

As used herein, and as further explained below, "pesticide" refers to a chemical substance, biological agent (such as a virus or bacterium), antimicrobial, disinfectant or device used against any pest. Pests include insects, plant pathogens, weeds, molluscs, birds, mammals, fish, nematodes (roundworms), and microbes that destroy property, spread disease or are a vector for disease or cause a nuisance. However, for the present invention by "pesticide" we mean that the pest is any invertebrate animal that destroys property, particularly agricultural commodities.

In an alternative embodiment, the invention may comprise the δ-amaurobitoxin-PI1a toxin, or a fragment or variant thereof.

The toxin δ-amaurobitoxin-PI1a is from the spider *Pireneitega luctuosa* and does not contain a predicted pro-region in its endogenous gene sequence. Surprisingly, the present inventors have found that including a pro-region (designed based on similar sequences present in the global database) in an expression construct for recombinant δ-amaurobitoxin-PI1a results in a recombinant toxin with increased biological activity against invertebrate pests. This unexpected finding demonstrates that the present invention can be used to increase the biological activity of recombinant toxins which do not contain pro-regions associated with their endogenous gene sequences by designing and incorporating pro-regions into expression constructs.

While not wishing to be bound by theory, it is believed that the inclusion of a pro-region in the nucleic acid construct, results in improved folding of the toxin when expressed in vitro.

By "fragment or variant" we include that the toxin sequence of the invention can vary from the naturally occurring sequence with the proviso that the fragment or variant substantially retains the biological activity of the toxin. By retain the biological activity of the toxin it is meant that the fragment and/or variant retains at least a portion of the pesticide activity as compared to the native toxin. Typically the fragment and/or variant retains at least 50%, such as 60%, 70%, 80% or 90% activity. In some instances the fragment and/or variant may have a greater pesticide activity than the native toxin. In some embodiments the fragment and/or variant may display an increase in another physiological feature as compared to the native toxin. For example, the fragment and/or variant may possess a greater half-life in vitro and/or in vivo, as compared to the native toxin.

By "variants" of a sequence we include insertions, deletions and substitutions, either conservative or non-conservative. In particular we include variants of the nucleotide sequence where such changes do not substantially alter the biological activity of the toxin. A skilled person would know that such sequences can be altered without the loss of biological activity. In particular, single changes in the nucleotide sequence may not result in an altered amino acid sequence following expression of the sequence. Furthermore, if changes in the nucleotide sequence result in the incorporation of an alternative amino acid, but wherein the physio-chemical properties of the respective amino acid(s) are not substantially changed (for example, conservative substitutions such as Gly, Ala; Val, Ile, Leu; Asp, Glu; Asn, Gln; Ser, Thr; Lys, Arg; and Phe, Tyr), the functionality of the respective toxin should not be affected. Moreover small deletions within non-functional regions of the toxin can also be tolerated and hence are considered "variants" for the purpose of the present invention. "Variants" also include recombinant toxin proteins in which the amino acids have been post-translationally modified, by for example, glycosylation, or disulphide bond formation. The experimental procedures described herein can be readily adopted by the skilled person to determine whether a "variant" can still function as a toxin.

It is preferred if the variant has a sequence which has at least 75%, yet still more preferably at least 80%, in further preference at least 85%, in still further preference at least 90% and most preferably at least 95% or 97% identity with the "naturally occurring" nucleotide sequence of the toxin.

In a preferred embodiment, the present invention relates to arthropod toxins. The arthropod toxins investigated by the present inventors are small, cysteine-rich proteins belonging to several superfamilies of protein sequences. The gene sequences of some of these toxins contain sequences which are not present in the final protein product. These additional sequences include a predicted N-terminal signal peptide which is removed during translation, and a predicted pro-region, between the signal peptide and the final sequence of the protein as isolated (see FIG. 1A).

Most cysteine-rich small peptide toxins are initially translated as larger precursors (70-120 amino acids) which contain a conserved N-terminal signal peptide (of approximately 20 amino acids), removed during translation, a pro-region (of approximately 15-60 amino acids) which shows significant sequence conservation within protein families, and a C-terminal toxin-encoding region which gives rise to the mature toxin and is more variable.

Pro-regions have been predicted from cDNA sequences encoding many toxins, and are generally less variable than the mature toxin sequences when compared between members of protein families, although sequence motifs like those found in signal peptides have not been identified. The pro-region is, however, often rich in acidic amino acid residues (Tedford et al., 2004). For example, the amino acid sequence of the pro-region associated with ω-ACTX-Hv1a toxin is:

```
                                    (SEQ ID NO: 1)
EDTRADLQGGEAAEKVFRR (see also FIG. 1B)
```

The amino acid sequence of the pro-region associated with Ao1b toxin is:

```
                                    (SEQ ID NO: 2)
ISYEEGKELFQKER
```

Pro-regions can be identified by comparing the sequence determined for a protein isolated from its normal source with the sequence predicted by the gene encoding it. Such a comparison can show whether a proteolysis or cleavage step has taken place co- or post-translationally to obtain the final protein product. Pro-regions are removed from the N-terminus of a mature protein; however, they differ from signal peptides which are involved in routing polypeptides into secretory pathways. Signal peptides can be identified using a software algorithm such as SignalP* (Nielsen et al., 1997) based on the protein sequence predicted by the gene. To identify a pro-region, the directly determined protein sequence is first compared to the predicted sequence to show that a region is removed from the N-terminus; the presence of a signal peptide is then determined by prediction from the software; the pro-region can then be identified as the sequence region between the signal peptide and the mature protein N-terminus. Pro-regions in arthropod toxins can be predicted, based on the concepts outlined above, using software (SpiderP) freely available on the Arachnoserver database (www.arachnoserver.org/spiderP.html; Wong et al., 2013). This support vector machine (SVM) method utilises a specifically designed algorithm to combine both local and global sequence information.

Pro-regions identified using the abovementioned methods can be utilised in the present invention. The pro-region of the abovementioned aspects of the invention may be associated with the toxin of the invention in its naturally occurring sequence. Alternatively, the sequence of a pro-region may be designed based on the sequences available in global databases, or identified based on the abovementioned methods, and incorporated into nucleic acid constructs of toxins which are not associated with pro-regions normally (i.e. in the naturally occurring sequence) or associated with a different pro-region in the naturally occurring sequence.

In an embodiment of the invention, the pro-region comprises the amino acid sequence EDTRADLQGGEAAEKVFRR (SEQ ID NO: 1), or a fragment or variant thereof.

In a further embodiment of the invention, the pro-region comprises the amino acid sequence ISYEEGKELFQKER (SED IQ NO: 2), or a fragment or variant thereof.

By "fragment or variant" of the pro-region we include that the nucleic acid sequence of the pro-region can differ from that known in the art and that naturally occurring, with the proviso that the fragment or variant substantially retains the biological activity of the pro-region i.e. it is still capable of improving the biological activity of the toxin with which it is associated.

In the accompanying examples, the inventors have shown that the pro-region may be removed during expression, such that it is not present in the final protein or fusion protein. However, it should be appreciated that a protein/fusion protein in which the pro-region is retained following expression still falls within the scope of the present invention.

The nucleic acid constructs according to abovementioned aspects of the invention, and any embodiments thereof, may also contain the sequence of a protein capable of mediating translocation of the protein produced from the construct from the invertebrate gut (a "carrier" protein) or a fragment or variant thereof. Such sequences may be fused to the toxin protein sequence, thereby generating a fusion protein. Any protein which binds to the insect gut can be used as a carrier protein, providing it is stable under the conditions found in the gut and is non-toxic to mammals.

Suitable proteins capable of functioning as carrier proteins include lectins. Generally, any lectin which binds to the insect gut can be used. In one embodiment of the invention, the carrier proteins are plant lectins.

The inventors have previously shown that certain plant lectins are resistant to gut proteolysis and have the potential to act as carriers to deliver other peptides from the gut to the circulatory system of target species. The present inventors have also shown that fusing plant lectins to a toxin aids translocation across the gut wall of an invertebrate pest, thus increasing biological activity of the toxin, and enabling such a fusion protein to be utilised as a pesticide.

A preferred embodiment of the invention is wherein the carrier protein is a plant lectin selected from any one or more of the following: snowdrop lectin (GNA), garlic lectin *Allium sativum*, pea lectin *Pisum sativum* (P-lec), peanut lectin *Arachis hypogaea*, french bean lectin (PHA, *Phytohaemagglutinin*), or a fragment or variant thereof.

By "fragment or variant" of the plant lectin we include that the nucleic acid sequence of the particular lectin can differ from that known in the art and that naturally occurring, with the proviso that the fragment or variant substantially retains the biological activity of the lectin i.e. it is capable of mediating translocation of the fusion protein from the invertebrate gut.

In a preferred embodiment, the lectin is GNA. The inventors have surprisingly shown in the accompanying examples that a toxin protein produced from a nucleic acid construct containing the sequence of a toxin, in addition to a pro-region and the sequence of GNA, results in an increased biological activity against invertebrate pests compared to the toxin alone, a toxin coupled to GNA only and a toxin coupled to a pro-region only. While the addition of a pro-region, or a fusion to another protein could each be expected to enhance the biological activity of a recombinant toxin, a combination of both modifications would not be expected to produce an additive effect. It was considered that both of these modifications would lead to the same result, namely correct protein folding, and thus either modification, or both, would lead to the same enhancement of biological activity. The inventors have shown that this is not the case.

As will be appreciated, a starting material for the production of a nucleic acid construct comprising (i) an arthropod toxin sequence, (ii) a pro-region and (iii) a carrier protein sequence is a nucleic acid construct consisting of (i) a pro-region and (ii) a carrier protein sequence.

Accordingly, a fifth aspect of the invention comprises a nucleic acid construct comprising (i) a pro region, or fragment or variant thereof and (ii) a sequence of a protein capable of mediating translocation of a protein produced from the construct from the invertebrate gut (a carrier protein), or a fragment or variant thereof.

The pro-region and carrier protein can be any pro-region/carrier protein discussed in relation to the abovementioned aspects of the invention.

Methods of preparing nucleic acid constructs use routine molecular biology techniques. A variety of methods have been developed to link polynucleotides to form continuous single or double strands, especially double-stranded DNA, for example via complementary cohesive termini produced by digestion with restriction enzymes. Suitable methods are described in Sambrook & Russell, Molecular Cloning: A Laboratory Manual: $3^{rd}$ edition. Such methods can be readily used by the skilled person to prepare a nucleic acid molecule according to the second aspect of the invention. Moreover, the accompanying examples provide further details as to how such molecules are prepared.

A desirable way to prepare the nucleic acid constructs of the invention is to use the polymerase chain reaction. This method may be used for introducing the DNA into a suitable vector, for example by engineering suitable sites for digestion by restriction enzymes, or it may be used to modify the DNA in other useful ways as is known in the art.

In an embodiment of the invention, the nucleic acid constructs according to the abovementioned aspects of the invention, and embodiments thereof, are expression constructs.

An "expression construct" is a term well known in the art. Expression constructs are basic tools for the production of recombinant proteins in biotechnology. The expression construct generally includes a plasmid that is used to introduce a specific nucleic acid sequence into a target cell, a "host cell". Once the expression construct is inside the cell, protein that is encoded by that nucleic acid sequence is produced by the cellular-transcription and translation machinery ribosomal complexes. The plasmid may also include nucleic acid sequences required for maintenance and propagation of the vector, in some cases through integration into the host genome. The goal of an expression vector is the production of large amounts of stable messenger RNA, and therefore proteins.

The nucleic acid constructs of the invention may further comprise appropriate regulatory sequences, including promoter sequences, terminator fragments, enhancer sequences, marker genes and/or other sequences. For further details see, for example, Sambrook & Russell, Molecular Cloning: A Laboratory Manual: $3^{rd}$ edition.

The nucleic acid constructs may be further engineered to contain regulatory sequences that act as enhancer and promoter regions and lead to efficient transcription of the fusion protein sequence carried on the construct. Many parts of the regulatory unit are located upstream of the coding sequence of the heterologous gene and are operably linked thereto. The nucleic acid construct may further contain a downstream 3' untranslated region comprising a polyadenylation site, if expression in a eukaryotic host, for example *Pichia pastoris*, is envisaged. The regulatory sequences can direct constitutive or inducible expression of the heterologous coding sequence.

The methods used to join individual nucleic acid fragments to create the nucleic acid constructs of the invention, may introduce 2-4 extra amino acid residues at the N-terminus of the pro-region, and up to 12 amino acids at the C-terminus of the carrier protein. There may also be short "linker" regions between the toxin and carrier sequences. These additional amino acid residues maintain the coding sequence and do not affect activity of the toxins or fusion proteins.

As used herein, the term "biological activity" refers to the toxicity of the recombinant toxin to invertebrate pests. The calculation of biological activity may be based on the $LD_{50}$.

The incorporation of a pro-region into a nucleic acid construct for the expression of a recombinant toxin can result in at least a 25%, 50%, 100%, 200%, 300%, 400% or higher increase in the biological activity, compared to the biological activity of a recombinant toxin produced from a nucleic acid construct without a pro-region. In the present case, such a biological activity may be a pesticide activity, which can be measured by a variety of techniques, including pest death, reduced life span, reproduction limitation such as reduced fertility or egg production and the like.

The further incorporation of a sequence of a carrier protein, into an expression construct for the expression of a recombinant toxin can result in at least 25%, 50%, 100%, 200%, 300%, 400% or higher increase in the biological activity, compared to the biological activity of a recombinant toxin produced from a nucleic acid construct containing the toxin sequence and a pro-region.

The expression system of the present invention can be either prokaryotic or eukaryotic. Suitable expression systems include bacterial expression systems (for example *E. coli* and *Bacillus subtilis*), yeast expression systems (for example *Saccharomyces cerevisiae* and *Pichia pastoris*), filamentous fungi expression systems (for example *Aspergillus*), and plant, animal and insect cell expression systems. However, it is preferred that the expression system utilised is the yeast *Pichia pastoris*. *Pichia* protein expression systems are well known in the art, and consequently cells for use as host cells can be readily obtained.

The host cell of the present invention can be prokaryotic or eukaryotic. Preferred prokaryotic host cells are typically strains of *E. coli* such as, for example the *E. coli* strains DH5 and RR1. Preferred eukaryotic host cells include yeast, insect and mammalian cells, preferably vertebrate cells such as those from a mouse, rat, monkey or human fibroblastic cell lines. Yeast host cells include YPH499, YPH500 and YPH501 which are generally available from Stratagene Cloning Systems, La Jolla, Calif. 92037, USA. However, it is preferred that the host cell is the yeast *Pichia pastoris*. Picha protein expression systems are well known in the art, and hence cells for use as host cells can be readily obtained. Particularly preferred is where the cell strain is SMD1168H, which can be obtained from Invitrogen™.

Transformation of appropriate cell hosts with a nucleic acid construct is accomplished by well known methods that typically depend on the type of vector used. With regard to the transformation of prokaryotic host cells, see for example, Sambrook & Russell, Molecular Cloning: A Laboratory Manual: 3rd edition. Transformation of yeast cells is described in Sherman et al., 1986.

Electroporation is also useful for transforming and/or transfecting cells and is well known in the art for transforming yeast cells, bacterial cells, insect cells and vertebrate cells. Methods for transformation of yeast by electroporation are disclosed in Becker & Guarente, 1990.

Successfully transformed cells, i.e. cells that contain a nucleic acid construct according to the present invention, can be identified by well known techniques. For example, cells resulting from the introduction of a nucleic acid construct of the present invention can be grown to produce a toxin fusion protein. Cells can be harvested and lysed and their DNA content examined for the presence of the DNA such as that described by Southern, 1975 or Berent et al., 1985.

Thus, in addition to the transformed host cells themselves, the present invention also contemplates a culture of those cells, preferably a monoclonal culture, or a culture derived from a monoclonal culture, in a nutrient medium.

An embodiment of the abovementioned aspects of the invention is wherein the nucleic acid construct further comprises a sequence which encodes an affinity tag to aid recovery and purification of the toxin protein, once expressed.

The use of short amino acid tag sequences to aid the affinity purification of recombinant proteins is well known in the art. Indeed, many commercially available protein expression constructs include nucleic acid sequences encoding such tags. The protein of interest is inserted in to the expression construct in such a manner that the affinity tag is linked to said protein. A variety of different affinity tags are known in the art, including chitin binding protein (CBP), maltose binding protein (MBP), glutathione-S-transferase (GST), and the polyhistidine-tag (His-tag).

A His-tag is an amino acid motif in proteins that consists of at least five histidine (His) residues, often at the N- or C-terminus of the protein. It is also known as hexa histidine-tag, 6×His-tag, and by the trademarked name His-tag®. They are a well known affinity tag and methods of introducing His-tags to recombinant proteins are known in art, as are routine methods of purifying proteins with His-tags. A preferred embodiment of the invention is wherein the additional affinity tag sequence encodes a His-tag.

The method of the fourth aspect of the invention may further comprise culturing the host cell as described in the third aspect of the invention (and any embodiment thereof described in this specification) for a sufficient time and under appropriate conditions in a culture medium so as to obtain expression of the fusion protein.

Methods of cultivating host cells and isolating recombinant proteins are well known in the art. Examples of suitable purification techniques are described in the accompanying examples. As described above, the fusion protein may comprise an affinity tag so as to aid purification using affinity reagents, as will be know to those skilled in the art.

The recombinant toxin protein with increased biological activity according to the present invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatograph, hydroxylapatite chromatography and lectin chromatography.

Alternatively the recombinant toxin protein with increased biological activity according to the present invention may be recovered from the supernatant. In this case, the host cell is removed from the supernatant by simple centrifugation as would be appreciated by a person skilled in the art. The protein can be isolated from the culture medium using standard techniques known in the art such as the abovementioned techniques.

The inventors have determined that the recombinant toxin protein with increased biological activity according to the present invention can be used as a pesticide.

A sixth aspect of the invention provides a pesticide composition comprising a toxin protein produced according to the first or fourth aspects of the invention and any embodiment thereof described in this specification.

A pesticide may be a chemical substance, biological agent (such as a virus or bacterium), antimicrobial, disinfectant or device used against any pest. Pests include insects, plant pathogens, weeds, molluscs, birds, mammals, fish, nematodes (roundworms), and microbes that destroy property, spread disease or are a vector for disease or cause a nuisance. However, for the present invention by "pesticide" we mean that the pest is any invertebrate animal that destroys property, particularly agricultural commodities.

More preferably still the toxin protein is capable of destroying, or at least debilitating, insect pests from the following orders: Coleopterans e.g. Southern corn rootworm (*Diabrotica undecimpunctata*); cowpea bruchid (*Callosobruchus maculatus*); Lepidopterans e.g. European cornborer (*Ostinia nubilalis*); tobacco hornworm (*Manduca sexta*); stem borer (*Chilo partellus*): Homopteran pests e.g. Rice brown plant hopper (*Nilaparvata lugens*); rice green leaf hopper (*Nephotettix cinciteps*); potato leaf hopper (*Empoasca fabae*); peach potato aphid (*Myzus persicae*); pea aphid (*Acyrthosiphon pisum*); Dipteran e.g. gout fly Chlorop pumilionis; Orthoptera e.g. crickets and locusts; Isoptera e.g. termites; Thysanoptera e.g. thrips; Hymenoptera e.g. ants and arthropod pests of the order Acarina (mites).

Particularly preferred pests include the Lepidopteran *Mamestra brassicae*, Colorado potato beetle (*Leptinotarsa decemlineata*, a Coleopteran), Wheat bulb fly (*Delia coarctata*, an Anthomyiidae) and the cereal aphid *Sitobion avenae*, a Homopteran.

The inventors have also investigated whether recombinant toxin proteins with increased biological activity produced according to the methods of the present invention have pesticidal activity against molluscs. As demonstrated in the accompanying examples, they have surprisingly found that the grey field slug (*Decoceras reticulatum*, a mollusc) is susceptible to the pesticidal activity of a recombinant toxin protein produced according to the present invention. Accordingly, a recombinant toxin protein according to the present invention is capable of destroying, or at least debilitating, molluscs, including slugs and snails, and particularly grey field slugs.

Preferably the pesticidal composition according to the invention is in the form of any desired formulation such as a solution, emulsion, spray, suspension, powder, foam, paste, granule, aerosol, capsule or other finely or coarsely divided material or impregnant for natural or synthetic material.

In a preferred embodiment the pesticidal composition is in the form of a spray, suspension or the like, in admixture with suitable diluents, adjuvents, preservatives, dispersants, solvents, emulsifying agents or the like. Suitable composition components are those conventionally employed in the art, and in particular being suited to the present oral administration application. The composition may be obtained with use of any suitable solvents, preferably water, alcohol, mineral oil or the like, any suitable solid carriers such as kaolin, clay, talc, chalk, quartz, attapulgite, montmorillonite, diatomaceous earth, silica, or the like, with use of any solid carriers as supports for granules such as calcite, marble, pumice and crushed natural fibre material or the like.

Compositions for use in the invention may additionally be employed in intimate or physical admixture together with other known insecticides, growth promoting or regulating substances, herbicides, fungicides, synergistic agents and the like.

The composition is preferably suitable for physically or chemically associating with plants or their locus and for oral uptake by pathogens.

The composition may therefore comprise a fusion protein (toxin) in an amount of between 0.001% and 99% by weight preferably between 0.5% and 98% by weight, more preferably between 1.0% and 95% by weight.

The term "locus" as used above refers to the physical location where the crop or plant is growing. For example, for agricultural crops, the locus may be a field; for vegetable crops, the locus may be a flowerbed or vegetable patch; and for ornamental plants, the locus may be a flower pot or container.

A seventh aspect of the present invention provides a process for the preparation of a pesticide composition according to the sixth aspect of the invention (and any embodiment thereof described in this specification) which comprises admixture of an amount of toxin protein with increased biological activity produced according to the present invention (and any embodiment thereof described in this specification) with one or more suitable carriers, diluents, adjuvants, preservatives, dispersants, solvents, emulsifying agents in effective pesticidal amount.

An eighth aspect of the present invention provides a method of preventing or treating a pest infection of a plant comprising applying a quantity of the toxin protein with increased biological activity produced according to the present invention or a pesticide composition according to the sixth aspect of the invention (and any embodiment thereof described in this specification) to the plant or its locus of growth; or introducing to the plant the nucleic acid construct according to the present invention.

A range of different mollusc pests can be controlled using the method of the eighth aspect of the invention, particularly the grey field slug (*Decoceras reticulatum*). Accordingly, the method of the eighth aspect of the invention includes where the mollusc is a slug or snail, and particularly a grey field slug.

A ninth aspect of the present invention provides a method of preventing or treating a mollusc pest infection of a plant comprising applying a quantity of toxin protein with increased biological activity produced according to the present invention, or a pesticide composition according to the sixth aspect of the invention (and any embodiment thereof described in this specification) to the plant or its locus of growth, or introducing to the plant a nucleic acid construct according to the present invention.

The toxin protein with increased biological activity produced according to the present invention and the related aspects and embodiments of the invention listed above, in particular the pesticide compositions, can be used as molluscicide.

It will be appreciated that the molluscicide are suitably prepared and formulated so as to allow easy use by the consumer. For example, the molluscicide may be prepared as a liquid which can be sprayed on a crop, or as granules that can also be applied to crops and/or locus.

It is well known in the art that molluscicides are commonly presented in the form of bait (or pellets). When presented in such a format, the user can easily apply the molluscicde to the plant or its locus of growth and so prevent or treat mollusc pest infection.

A tenth aspect of the invention therefore provides a molluscicide bait composition comprising a toxin protein with increased biological activity produced according to the present invention and/or a pesticide composition according to the sixth aspect of the invention.

The pellet or bait can also include a mollusc attractant so as to encourage exposure of the pest to the molluscicide. A mollusc attractant is anything that attracts molluscs. The attractant may be a phagostimulant. Phagostimulants are conventionally used in slug and snail bait formulations to attract gastropods to ingest the molluscicide, and are typically attractants and/or food. Mixtures of phagostimulants with other suitable organic and/or inorganic carriers may also be used. Suitable phagostimulants for molluscicides include ground cereals (such as wheat flour, barley flour, rye flour and rice starch), crushed soya beans, fish meal, molasses, crushed rapeseed and the like. Mixtures of phagostimulants may also be used in the present invention. Other known attractants include beer, yeast and extract of dead slugs. The bait composition may also comprise one or more bird repellents, such as anthraquinone.

The composition may be formulated to provide a slow or delayed release of molluscicide over time, so as to provide long-term protection against molluscs. Suitable slow-release auxiliaries which may be employed in the formulation include, for example, resins (such as urea/formaldehyde resins), soyabean meal, waxes, stearates and oils (such as castor oil).

Other auxiliaries that may be used in the bait or pellet composition of the present invention include, for example, binders (such a methylcelloslove, polyvinylpyrrolidone, polyvinyl alcohol, polyacrylates, polymethacrylates, natural waxes, chemically modified waxes and synthetic waxes, sugars, starch, alginates, agar, lignosulphonates and gum Arabic), humectants (such as polyalcohols, for example sugars or glycerol), preservatives, colorants and repellents for warm-blooded species.

The bait composition may also be coated to protect it from moisture degradation. Such a coating may extend the life of the bait composition, and reduce the re-application frequency needed. Suitably the bait composition does not prematurely degrade when it is applied to damp soil.

The bait composition is typically provided in the form of granules or pellets. The size of the pellets is such that they can be readily consumed by the target gastropods to ensure ingestion. Typically, the pellets are from about 1 mm to about 5 mm in length.

An eleventh aspect of the invention provides a transgenic plant or progeny thereof comprising a nucleic acid construct according to the present invention capable of expressing a toxin in accordance with the present invention.

By "transgenic plant" we include that the plant may have a nucleic acid construct according to the present invention incorporated into its germline or that the plant may contain an exogenous nucleic acid construct according to the present invention, either of which can be expressed in the plant.

It will be appreciated that a transgenic plant containing a nucleic acid construct according to the invention, when regulated in the correct manner, will produce a toxin protein with increased biological activity according to a method of the invention. The protein/fusion protein produced will function as a pesticide.

A range of different plant species can be modified to include the nucleic acid construct according to the present invention.

A person skilled in the art would know that any monocot or dicot plant can be used. A dicot plant may be selected from the families including, but not limited to Asteraceae, Brassicaceae (e.g. *Brassica napus*), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae For example, the plant may be selected from lettuce, sunflower, *Arabidopsis*, broccoli, spinach, water melon, squash, cabbage, tomato, potato, capsicum, tobacco, cotton, okra, apple, rose, strawberry, alfalfa, bean, soybean, field (fava) bean, pea, lentil, peanut, chickpea, apricots, pears, peach, grape vine or citrus species.

Also included are biofuel and bioenergy crops such as sugar cane, oilseed rape/canola, linseed, willow, poplar, poplar hybrids, switchgrass, *Miscanthus* or gymnosperms, such as loblolly pine. Also included are crops for silage (e.g. forage maize), grazing or fodder (e.g. grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed).

A monocot plant may, for example, be selected from the families Arecaceae, Amaryllidaceae or Poaceae. For example, the plant may be a cereal crop, such as wheat, rice, barley, maize, oat, sorghum, rye, onion, leek, millet, buckwheat, turf grass, Italian rye grass, switchgrass, *Miscanthus*, sugarcane or *Festuca* species.

Preferably, the plant is a crop plant. By crop plant is meant any plant which is grown on a commercial scale for human or animal consumption or use or other non-food/feed use. Preferred plants are maize, tobacco, wheat, rice, oilseed rape, sorghum, soybean, potato, tomato, barley, pea, bean, field bean, cotton, lettuce, broccoli or other vegetable brassicas.

The nucleic acid construct can be introduced as a transgene into the plant. This can be carried out by various methods as known in the field of plant genetic engineering, for example using transformation with *Agrobacterium*, particle bombardment, electroporation or viral transformation. Such techniques are well known in the art. The use of specific techniques for each of the plant species listed herein are also well known. The methods of the art can be readily adopted by the skilled person to prepare a transgenic plant or progeny thereof comprising a nucleic acid sequence according to the invention.

When used for preparing a transgenic plant of this aspect of the invention, the nucleic acid construct is typically placed within an "expression cassette" suitable for arranging the expression of the nucleic acid sequence in the plant. The expression cassette will typically contain nucleic acid sequence which act to regulate the expression of the nucleic acid in the plant, e.g. a promoter region.

Some promoters can drive constitutive expression of the nucleic acid in plants, including the well known 35S promoter, 19S promoter or the ubiquitin promoter.

Other promoters can be used to regulate organ or tissue specific expression of the nucleic acid construct. A "tissue-specific promoter" or "tissue-preferred promoter" refers to a regulated promoter that is not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of sequence. Suitable promoters include the napin-gene promoter from rapeseed, the USP-promoter from *Vicia faba*, the oleosin-promoter from *Arabidopsis*, the phaseolin-promoter from *Phaseolus vulgaris*, the Bce4-promoter from *Brassica* or the legumin B4 promoter as well as promoters conferring seed specific expression in monocot plants.

Promoters active in photosynthetic tissue in order to drive transcription in green tissues such as leaves and stems include ribulose-1,5-bisphosphate carboxylase (RbcS) promoters such as the RbcS promoter from eastern larch (*Larix laricina*), the pine cab6 promoter, the Cab-1 gene promoter from wheat, the CAB-1 promoter from spinach, the cablR promoter from rice, the pyruvate orthophosphate dikinase (PPDK) promoter from corn, the *Arabidopsis thaliana* SUC2 sucrose-H+ symporter promoter. Nucleic acid sequences representative of such promoters can be readily identified by the skilled person from, for example, GenBank.

Promoters suitable for preferential expression in plant root tissues include, for example, the promoter derived from corn nicotianamine synthase gene and rice RCC3 promoter.

Promoters suitable for preferential expression in plant vascular tissues include, for example, rice sucrose synthase-1 gene (RSs1).

Inducible promoters include promoters which are responsive to abiotic and biotic environmental stimuli. Abiotic environmental stimuli include light, temperature and water availability. Biotic environmental stimuli include pathogens, (including viral induced, bacterial induced, fungal induced, insect induced and nematode induced promoters), interactions with symbionts and herbivores. Promoters may also be responsive to movement, touch, tissue damage and phytohormones (including abscissic acid, cytokinins, auxins, giberellins, ethylene, brassinosteroids and peptides such as systemin and nodulation factors). Temporally regulated promoters include circadian regulated promoters as well as those which respond to non-circadian time-keeping mechanisms.

Chemically inducible promoters are especially suitable if gene expression is wanted to occur in a time specific manner. Examples of such promoters are a salicylic acid inducible promoter, a tetracycline inducible promoter, and an ethanol inducible promoter (WO 93/21334).

In order to obtain improved expression in plants, the codon usage of the nucleic acid construct can be modified to form an equivalent, modified or artificial gene or gene part in accordance with techniques, so as to increase the efficiency of expression of the toxin protein in plant cells. Moreover, the nucleic acid may also be inserted in the plastid (e.g. chloroplast) or mitochondrial genome of a plant and expressed there using a suitable promoter. For obtaining enhanced expression in monocot plants such as corn or rice, an intron (e.g. a monocot intron) can also be added to the chimeric gene.

It may be preferred that chimeric nucleic acids of the invention (and suitable for use in the methods of the invention) further comprise nucleic acid sequences for the expression of products that may aid in the identification of plant cells into which the chimeric nucleic acid sequences have been successfully incorporated. Examples of suitable further nucleic acid sequences that may be used in this manner will be apparent to those skilled in the art, and include nucleic acids giving rise to products that confer resistance to substances that may be used for selection (such as antibiotics) or markers that give rise to a detectable product that may be used as the basis for selection (such as a chromogenic enzyme product).

A further aspect the present invention provides a plant transformed with a nucleic acid construct according to the present invention.

In a further aspect the present invention provides a plant seed comprising a nucleic acid construct according to the present invention.

A further aspect of the invention provides the use of a nucleic acid construct according to the present invention or a toxin protein produced according to the present invention in the manufacture of a pesticide or a transgenic plant cell or plant.

A further aspect of the invention provides the use of a pesticide according to the sixth aspect of the present invention (and any embodiment thereof described in this specification) to destroy, or debilitate one or more pests.

A further aspect of the invention provides a nucleic acid construct, toxin protein, composition, vector, host cell, transgenic plant, or methods for the preparation or use thereof substantially as herein described in the description or sequences or illustrated in the Figures.

DETAILED DESCRIPTION

The present invention will now be described with reference to the following non-limiting examples and figures, which show:

FIG. 1: Schematic of gene structure of toxins containing pro-regions (A) Schematic of gene structure of toxin proteins containing pro-regions. (B) Sequence of spider toxin (SED ID NO: 19), Hv1a. Boxed amino acid sequence corresponds to pro-region.

FIG. 2: Expression and purification of recombinant Hv1a and pro-Hv1a toxin (A) SDS-PAGE gel (20% acrylamide) analysis showing purification of recombinant Strep-tagged Hv1a toxin from culture supernatant. Lanes 1 & 2 are GNA standards (0.5 and 0.25 μg, respectively) and lanes 3 & 4 are peak fractions (10 μl) following elution from Streptactin column with 2.5 mM desthiobiotin. (B) Tris-Tricine gel (15% acrylamide) analysis of recombinant pro-Hv1a, lanes 1 & 2 are peak fractions (10 μl) following elution from a nickel affinity column with 0.2 M imidazole. Arrow depicts major protein product predicted to be pro-Hv1a from which the histidine tag has been cleaved. (C) Western blot analysis of sample in (B) using anti-His antibodies.

Figure 3:
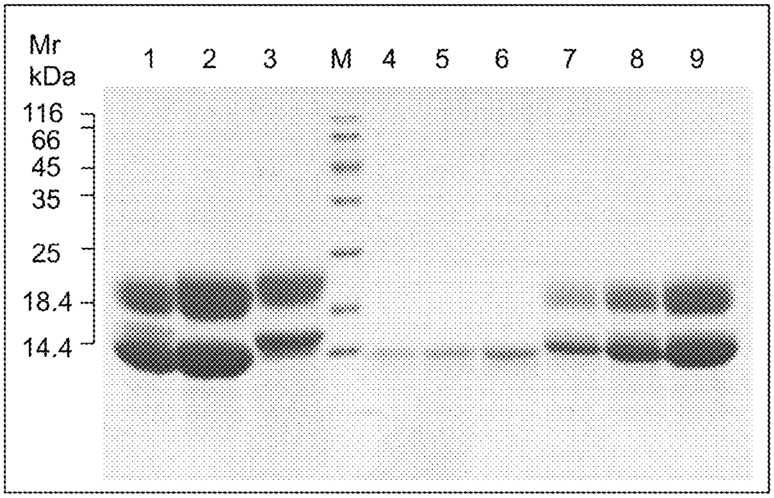

FIG. 3: SDS-PAGE gel analysis of lyophilised samples of purified pro-Hv1a/GNA, Hv1a/GNA and MODHv1a/GNA SDS-PAGE analysis (17.5% acrylamide gel) of purified recombinant Hv1a containing fusion protein, gel stained for total proteins with Coomassie Blue. Loading as follows: Lane 1: pro-Hv1a/GNA; Lane 2: Hv1a/GNA; Lane 3: MODHv1a/GNA; Lanes 4-6: GNA standards of 1, 2 and 4 μg, respectively; Lanes 7-9: 12.5, 25 and 50 μg lyophilised purified pro-Hv1a/GNA (to enable quantification of fusion protein content).

FIG. 4: Injection toxicity of recombinant pro-Hv1a, pro-Hv1a/GNA and Hv1a/GNA to *Mamestra brassicae*

Percentage survival of 3rd-5$^{th}$ instar *Mamestra brassicae* larvae following the injection of different doses of recombinant pro-Hv1a, pro-Hv1a/GNA or Hv1a/GNA. (A) Percentage survival of 5$^{th}$ instar larvae following injection of various doses of pro-Hva1. (B) Percentage survival of 3$^{rd}$-4$^{th}$ instar larvae following injection of various doses of pro-Hv1a/GNA (Dose A) or Hv1a/GNA (Dose B). (C) Percentage survival of 5$^{th}$ instar larvae following injection of various doses of pro-Hv1a/GNA (Dose A) and Hv1a/GNA (Dose B).

Figure 5:
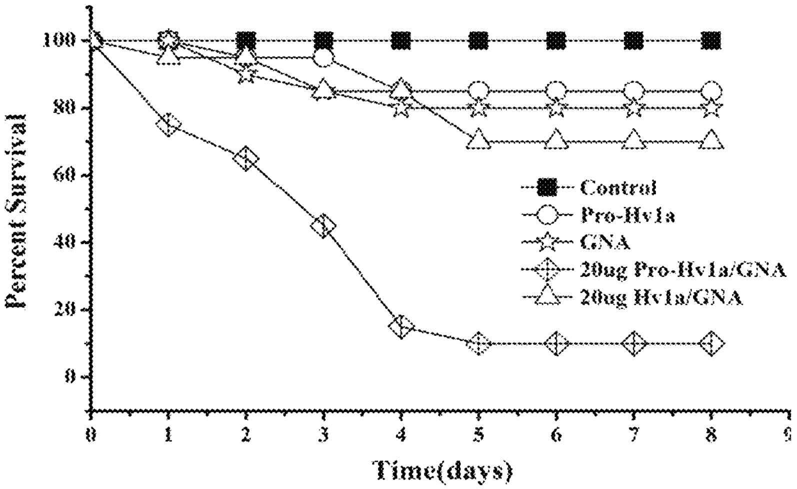

FIG. 5: Ingestion toxicity of recombinant pro-Hv1a, Hv1a/GNA, pro-Hv1a/GNA and GNA to *Mamestra brassicae*

Percentage survival of 3$^{rd}$ instar *Mamestra brassicae* larvae following ingestion of a single 2 μl droplet containing 20 μg of purified pro-Hv1a, Hv1a/GNA, pro-Hv1a/GNA or GNA. Control larvae were fed on a droplet containing no added protein (n=10 per treatment).

FIG. 6: Ingestion toxicity of recombinant pro-Hv1a, pro-Hv1a/GNA, Hv1a/GNA or GNA to *Acyrthosiphon pisum* and *Sitobion avenae*

Percentage survival of (A) *Acyrthosiphon pisum* (pea aphids) and (B) *Sitobion avenae* (cereal aphids) with artificial diets containing 0.05-0.75 mg/ml purified recombinant pro-Hv1a, pro-Hv1a/GNA, Hv1a/GNA or GNA.

Figure 7:
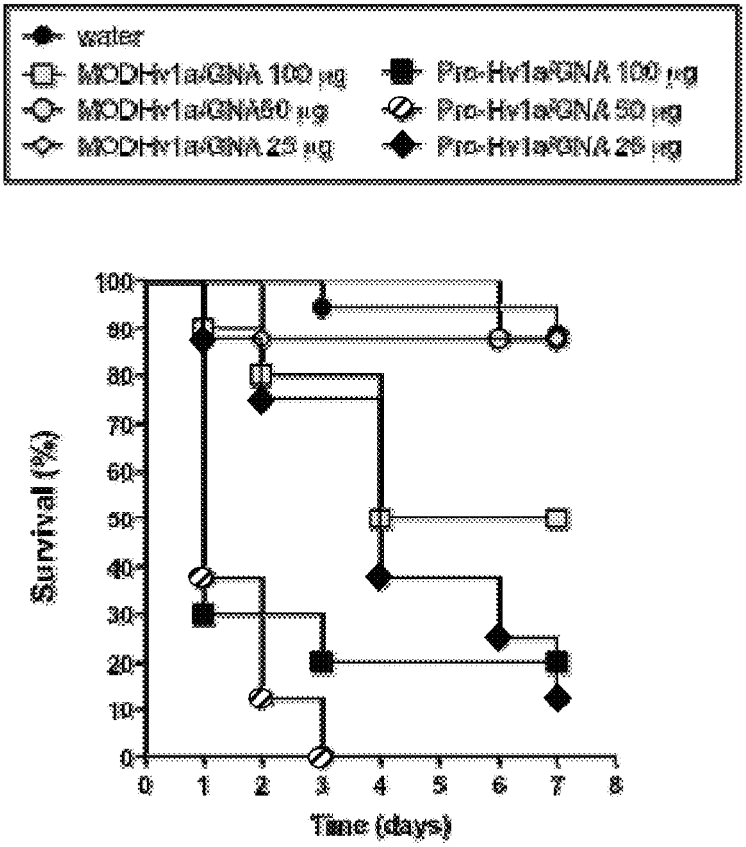

FIG. 7: Injection toxicity of recombinant pro-Hv1a/GNA and Hv1a/GNA to *Deroceras reticulatum*

Percentage survival of *Deroceras reticulatum* (200 mg±40 mg) injected with 100, 50 or 25 μg of Hv1a/GNA or pro-Hv1a/GNA. n=18 for control treatment; n=10 for 100 μg dose; and n=8 for 50 and 25 μg doses.

FIG. 8: Expression and purification of recombinant PI1a and Ao1bPro-PI1a toxin (A) PI1a toxin derived from a construct encoding the mature toxin sequence separated on "normal" SDS-PAGE; M indicates marker, loadings of PI1a are 5 and 10 μg. (B) PI1a toxin (5 μg) separated on SDS-PAGE after denaturation by 6 M urea. (C) Recombinant PI1a toxin derived from a construct containing the pro-region designated Ao1b on SDS-PAGE, loadings of Ao1bPro-PI1a are 2.5 μg. (D) Western blotting of purified Ao1bPro-PI1a (25, 50 & 100 ng) using anti-His antibodies.

FIG. 9: Characterisation of purified recombinant PI1a/GNA fusion proteins by SDS-PAGE (A) SDS-PAGE analysis of PI1a/GNA fusion protein (10 μg) and GNA standard (5 μg). (B) Deglycosylation of PI1a/GNA fusion protein using PNGase F (band indicated by open arrowhead), GNA standard (5 μg). (C) SDS-PAGE analysis of Ao1bPro-PI1a/GNA (1, 2 and 4 μg), GNA standard (5 μg). (D) SDS-PAGE analysis of Hv1aPro-PI1a/GNA (1, 2 and 4 μg), GNA standards (1, 2 and 4 μg).

FIG. 10: Injection toxicity of recombinant PI1a and Ao1bPro-PI1a to *Mamestra brassicae*

(A) Percentage survival of 5$^{th}$ instar *Mamestra brassicae* larvae following injection of different doses of purified recombinant PI1a. (B) Percentage survival of 5$^{th}$ instar *Mamestra brassicae* larvae following injection of different doses of purified recombinant PI1a (Dose A) or Ao1bPro-PI1a (Dose B).

FIG. 11: Injection toxicity of recombinant PI1a/GNA, Ao1bPro-PI1a/GNA and Pro-HV1a-PI1a/GNA to *Mamestra brassicae*

Percentage survival of 5$^{th}$ instar *Mamestra brassicae* larvae following injection of different doses of purified recombinant PI1a/GNA (A), Ao1b-ProPI1a/GNA (B) or Pro-Hv1a-PI1a/GNA (C). n=20 per treatment.

Figures 12A, 12B, 12C:
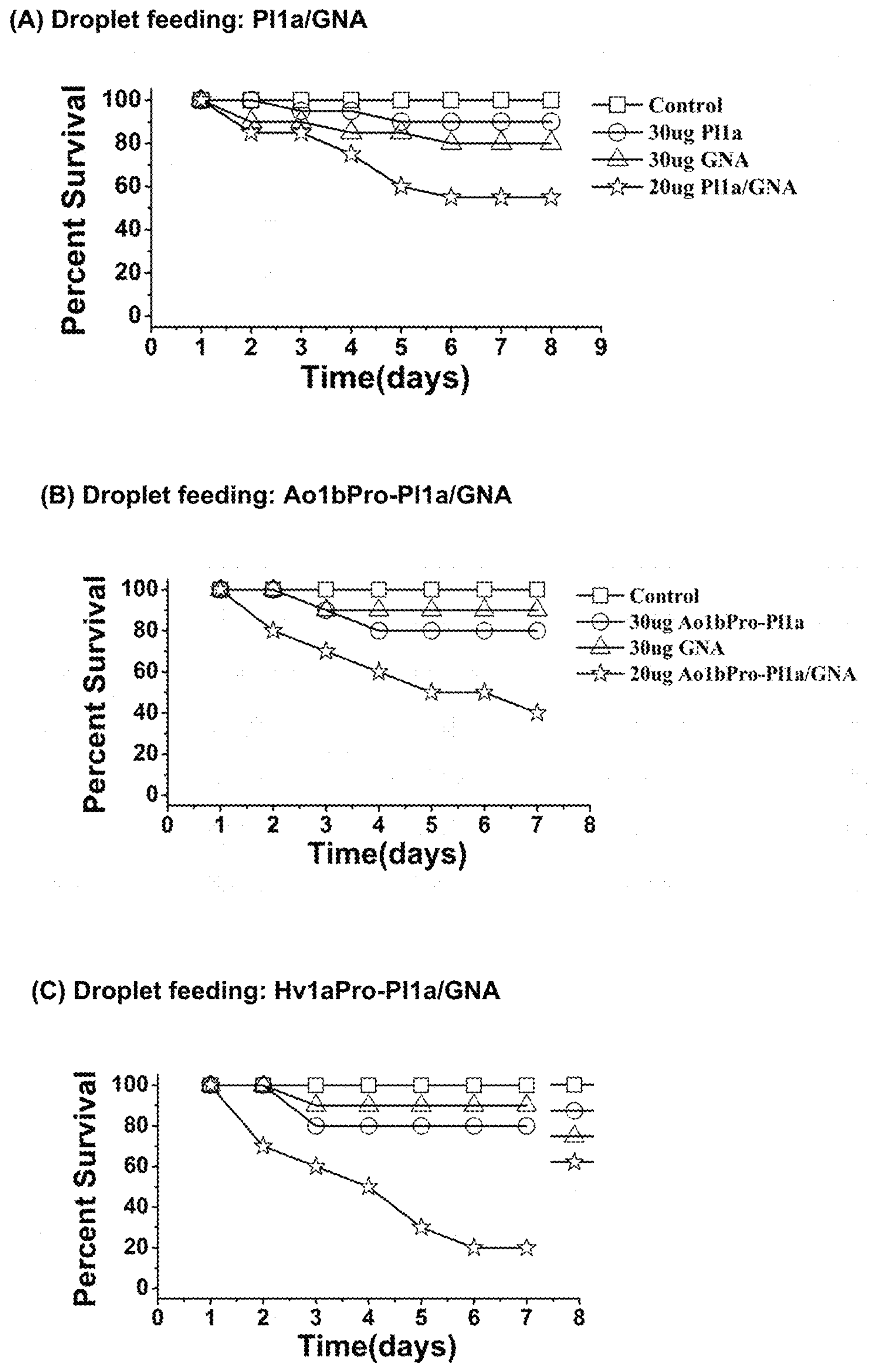

FIG. 12: Ingestion toxicity of recombinant PI1a/GNA, Ao1bPro-PI1a/GNA and Hv1aPro-PI1a/GNA to *Mamestra brassicae*

Percentage survival of 3$^{rd}$ instar *Mamestra brassicae* larvae following ingestion of a single 2 μl droplet containing 20 μg of purified PI1a/GNA (A), Ao1bPro-PI1a/GNA (B) or Hv1aPro-PI1a/GNA (C) fusion proteins. Controls in all cases were sucrose alone (no added protein); 30 μg of either PI1a toxin (mature or modified form) or GNA.

ABBREVIATIONS

BB: Binding buffer
ECL: Enhanced chemiluminescence
HRP: Horseradish peroxidase
PBS: Phosphate buffered saline
SDS-PAGE: Sodium dodecyl sulphate polyacrylamide gel electrophoresis
YPG: Yeast extract peptone glycerol Materials and Methods Cloning of Recombinant Hv1a, Pro-Hv1a and Pro-Hv1a/GNA Fusion Protein A synthetic gene encoding the mature Hv1a amino acid sequence was assembled using a series of overlapping oligonucleotides, with codon usage optimised for expression in yeast (Fitches et al., 2012). To create an expression construct coding for the mature Hv1a peptide the coding sequence was amplified by PCR using primers with PstI and SalI sites and purified from excised gel slices using a QiaQuick Gel Extraction Kit (Qiagen) as described in the manufacturer's protocol. The extracted DNA fragment was digested (PstI and SalI) and ligated into similarly digested yeast expression vector pGAPZαB (Invitrogen) that had been previously modified to contain a 5' Strep tag in frame with the yeast α-factor pre-pro-sequence. The resulting plasmid was transformed into electrocompetent *E. coli* cells and selected clones were checked for the correct assembly of the construct by gel electrophoresis and DNA sequencing.

The pro-Hv1a coding sequence was amplified by PCR using primers with Ps1I and XbaI sites (Forward: TACTGCAGCAGAAGATACTAGAGCT (SEQ ID NO: 3) and Reverse: ATTCTAGAATCACATCTCTTAAC (SEQ ID NO: 4). Gel extracted products were digested with Ps1I and XbaI and ligated into similarly digested yeast expression vector pGAPZaB. The resulting recombinant plasmid was transformed into *E. coli* and selected clones were checked for correct assembly of the construct by gel electrophoresis and DNA sequencing.

To produce the pro-Hv1a/GNA construct, the pro-Hv1a coding sequence was amplified by PCR using primers with PstI and NatI sites (Forward: TACTGCAGCAGAAGATACTAGAGCT (SEQ ID NO: 3)and Reverse: ATGCGGCCGCATCACATCTCTTAAC (SEQ ID NO: 5)) and purified by gel electrophoresis as described above. Following restriction by PstI and NotI, the PCR product was ligated into a previously generated pGAPZaB plasmid containing the mature GNA coding sequence digested with the same enzymes. Selected clones containing the expression vector encoding the pro-Hv1a/GNA fusion protein were verified by DNA sequencing.

The sequences of the Hv1a constructs are shown below:
Native Hv1a:

```
                                           (SEQ ID NO: 6)
SPTCIPSGQPCPYNENCCSQSCTFKENENGNTVKRCD
```

Recombinant Hv1a (alpha factor signal sequence, Hv1a toxin, Strep tag green highlighted region, no pro-region, no carrier):

```
                                           (SEQ ID NO: 7)
MRFPSIFTAVLFAASSALAAPVNTTTEDETAQIPAEAVIGYSDLEGDFDV

AVLPFSNSTNNGLLFINTTIASIAAKEEGVSLEKREAEAAWSHPQFEKGL

QSPTCIPSGQPCPYNENCCSQSCTFKENENGNTVKRCD
```

Recombinant pro-Hv1a (alpha factor signal sequence, Hv1a toxin, pro-region, no carrier, (His)$_6$ tag):

```
                                           (SEQ ID NO: 8)
MRFPSIFTAVLFAASSALAAPVNTTTEDETAQIPAEAVIGYSDLEGDFDV

AVLPFSNSTNNGLLFINTTIASIAAKEEGVSLEKREAEAAAEDTRADLQG

GEAAEKVFRRSPTCIPSGQPCPYNENCCSQSCTFKENENGNTVKRCDALE

QKLISEEDLNSAVDHHHHHH
```

Recombinant Hv1a/GNA (alpha factor signal sequence, Hv1a toxin, no pro-region, carrier):

```
                                           (SEQ ID NO: 9)
MRFPSIFTAVLFAASSALAAPVNTTTEDETAQIPAEAVIGYSDLEGDFDV

AVLPFSNSTNNGLLFI NTTIASIAAKEEGVSLEKRE-
AEAAASPTCI PSGQ

PCPYN ENCCSQSCTFKEN ENGNTVKRCDAAADNIL YSGETLSTGE-
FLNYG

SFVFI MQEDCNLVL YDVDKPIWATNT GGLSRSCFLSMQTDGNLV-
VYNPSN

KPIWASNTGGQNGNYVCILQKDRNVVIYGTDRWATGVD
```

Recombinant pro-Hv1a/GNA (alpha factor signal sequence, Hv1a toxin, pro-region, carrier, (His)$_6$ tag):

```
                                           (SEQ ID NO: 10)
MRFPSIFTAVLFAASSALAAPVNTTTEDETAQIPAEAVIGYSDLEGDFDV

AVLPFSNST 5 NNGLLFINTTIASIAAKEEGVSLEKREAEAAAEDTRADLQG

GEAAEKVFRRSPTCIPSGQPC PYN ENCCSQSCTFKEN ENGNTVKRCDAAA

DN IL YSG ETLSTGEFLNYGSFVFI MQEDCNLVL YDVDKPIWATNTGGLSR

SCFLSMQTDGNLVVYNPSNKPIWASNTGGQNGNYVCILQKDRNVVIYGTD

RWATGVDHHHHHH
```

Cloning of Recombinant PI1a and PI1a/GNA Fusion Proteins

A double stranded DNA incorporating a sequence encoding the mature PI1a toxin (P83256), with codon usage optimised for yeast, was designed by the inventors and synthesised and supplied by ShineGene Molecular Biotech, Inc. (Shanghai 201109, China; www.synthesisgene.com) in the vector pUC57. Other oligonucleotides were supplied by Sigma Chemical Co.

The PI1a coding sequence was transferred from pUC57 to the yeast expression vector pGAPZαB (Invitrogen) by digestion with PstI and XbaI, isolation of the coding sequence fragment by agarose gel electrophoresis, followed by ligation to pGAPZαB that had been digested with the same enzymes. DNA fragments were purified from excised gel slices using a QiaQuick Gel Extraction Kit (Qiagen). The resulting recombinant plasmid was cloned using standard protocols by transformation of electrocompetent *E. coli* cells. Selected clones were checked for correct assembly of the construct by DNA sequencing. To produce the modified construct for expression of PI1a two complementary synthetic oligonucleotides encoding the pro-region from U3-agatoxin-Ao1b (Q5Y4V7) were assembled and inserted into the PstI site of the PI1a expression construct. Correct assembly of the construct (ProAo1b-PI1a) was checked by DNA sequencing.

To produce a construct encoding the PI1a/GNA fusion protein, the mature PI1a coding sequence from a verified expression construct in pGAPZαB was excised by digestion with PstI and NotI and purified by agarose gel electrophoresis. A pGAPZαB plasmid containing the fusion protein construct Hv1a/GNA (Fitches et al., 2012) was digested with PstI and NotI to remove the Hv1a coding sequence and purified by agarose gel electrophoresis. The Hv1a coding region was subsequently replaced with PI1a by ligating the purified fragments and cloning the resulting recombinant plasmid. To produce the modified expression construct for PI1a/GNA containing the pro-region from U3-agatoxin-Ao1b, the PI1a/GNA expression construct was modified as described above; in addition, a pro-region from the pro-Hv1a toxin was also used in a further construct designated as Pro-Hv1a-PI1a. Selected clones containing the expression vector encoding the PI1a/GNA fusion proteins were verified by DNA sequencing. All DNA sequencing was carried out using Applied Biosystems ABI Prism 3730 automated DNA sequencers by DBS Genomics, School of Biological and Biomedical Sciences, Durham University, UK.

Native PI1a:

```
                                        (SEQ ID NO: 11)
    GCLGEGEKCADWSGPSCCDGFYCSCRSMPYCRCRNNS
```

Recombinant PI1a (alpha factor signal sequence, PI1a toxin, no pro-region, no carrier, $(His)_6$ tag):

```
                                        (SEQ ID NO: 12)
MRFPSIFTAVLFAASSALAAPVNTTTEDETAQIPAEAVIGYSDLEGDFDV

AVLPFSNSTNNGLLFINTTIASIAAKEEGVSLEKREAEAAAGCLGEGEKC

ADWSGPSCCDGFYCSCRSMPYCRCRNNSALEQKLISEEDLNSAVDHHHHH

H
```

Recombinant Ao1bPro-PI1a (alpha factor signal sequence, pro-region [Ao1b], PI1a toxin, no carrier, +$(His)_6$ tag):

```
                                        (SEQ ID NO: 13)
MRFPSIFTAVLFAASSALAAPVNTTTEDETAQIPAEAVIGYSDLEGDFDV

AVLPFSNSTNNGLLFINTTIASIAAKEEGVSLEKREAEAAAISYEEGKEL

FQKERGCLGEGEKCADWSGPSCCDGYCSCRSMPYCRCRNNSALEQKLISE

EDLNSAVDHHHHHH
```

Recombinant PI1a/GNA (alpha factor signal sequence, PI1a toxin, no pro-region, carrier, $(His)_6$ tag):

```
                                        (SEQ ID NO: 14)
MRFPSIFTAVLFAASSALAAPVNTTTEDETAQIPAEAVIGYSDLEGDFDV

AVLPFSNSTNNGLLFINTTIASIAAKEEGVSLEKREAEAAAGCLGEGEKC

ADWSGPSCCDGFYCSCRSMPYCRCRNNSAAADNIL YSGETLSTGEFLNYG

SFVFIMQEDCNLVL YDVDKPIWATN TGGLSRSCFLSMQTDGNLV-
VYNPSN

KPIWASNTGGQNGNYVCI LQKDRNVVIYGTDRWATGVDHHHHHH
```

Recombinant Ao1bPro-PI1a/GNA (alpha factor signal sequence, pro-region [Ao1b], PI1a toxin, carrier, $(His)_6$ tag):

```
                                        (SEQ ID NO: 15)
MRFPSI FTAVLFAASSALAAPVNTTTEDETAQI PAEAVI-
GYSDLEGDFDV

AVLPFSNSTNNGLLFINTTIASIAAKEEGVSLEKREAEAAAISYEEGKEL

FQKERGCLGEGEKCADWSGPSCCDGCSCRSMPYCRCRNNSAAADNILYSG

ETLSTGEFLNYGSFVFIMQEDCNLVL YDVDKPIWATNTGGLSRSCFLSMQ

TDGNLVVYNPSNKPIWASNTGGQNGNYVCILQKDRNVVIYGTDRWATGVD

HHHHHH
```

Recombinant Hv1aPro-PI1a/GNA (alpha factor signal sequence, pro-region [Hv1a], PI1a toxin, carrier, $(His)_6$ tag):

```
                                        (SEQ ID NO: 16)
MRFPSIFTAVLFAASSALAAPVNTTTEDETAQIPAEAVIGYSDLEGDFDV

AVLPFSNSTNNGLLFINTTIASIAAKEEGVSLEKREAEAAAEDTRADLQG

GEAAEKVFRRGCLGEGEKCADWSGPCCDGFYCSCRSMPYCRCRNNSAAAD

NIL YSGETLSTGEFLNYGSFVFIMQEDCNL VL YDVDKPIWATNTG-
GLSRS

CFLSMQTDGNLVVYNPSNKPIWASNTGGQNGNYVCILQKDRNVVIYGTDR

WATGVDHHHHHH
```

Expression of Hv1a, Pro-Hv1a, Hv1a/GNA and Pro-Hv1a/GNA Fusion Proteins in Yeast pGAPZαB plasmids containing Hv1a, pro-Hv1a, Hv1a/GNA and pro-Hv1a/GNA sequences were amplified in *E. coli*, purified and linearised with BlnI (Takara). Linearised plasmids were transformed into *Pichia pastoris* strain SMD1168H (Invitrogen) using the EasyComp Transformation kit (Invitrogen) as described in the manufacturer's protocol. Transformed yeast clones were selected on YPG agar plates (1% yeast extract (w/v), 2% peptone (w/v), 4% glycerol (v/v), 1.5% agar (w/v)) containing zeocin (100 mg/ml). Selected clones were checked for expression by analysis of culture supernatants from small-scale shake flask cultures (10 ml) grown for 2-3 days in YPG-zeocin media at 30° C. Supernatant samples were separated by SDS-polyacrylamide gel electrophoresis; gels were blotted onto nitrocellulose and probed with anti-$(His)_6$ primary antibodies (BioRad) or anti-Strep antibodies, or for Hv1a/GNA and pro-Hv1a/GNA blots were probed with anti-GNA primary antibodies, followed by washing, probing with HRP-conjugated secondary antibodies (BioRad), and detection of bound antibodies by ECL, as described previously (Fitches et al., 2001; 2012).

For protein production selected *P. pastoris* clones containing the integrated Hv1a, pro-Hv1a, Hv1a/GNA and pro-Hv1a/GNA expression cassettes were grown in either a 7.5 L BioFlo 110 bench-top fermenter (New Brunswick Scientific) or a 5 L Bio-Controlly ADI1010 bench-top fermenter (APPLIKON BIOTECHNOLOGY, Holland). YPG cultures (200 ml) of transformed *P. pastoris* were grown for 2-3 days at 30° C. with shaking (no zeocin antibiotics) before inoculating 2.5 L of sterile minimal media supplemented with PTM1 salts. Cultivation at 30° C., 30% dissolved oxygen, pH 4.5-5.0 with continuous agitation was carried out with a ramped glycerol feed (5-10 ml/h; total 1.25 l) over a period of 4 days. Culture supernatant was subsequently separated from cells by centrifugation (20 min, 8000 rpm; 4° C.), clarified by filtration through 2.7 μM and 0.7 μM glass fibre filters (GFD and GFF; Whatmann). For Hv1a only supernatant was adjusted to 50 mM phosphate buffer containing 0.3 M sodium chloride at pH 8.0 by adding 4× concentrated stock. Recombinant Hv1a was purified on streptactin columns (1 ml) with a flow rate of 0.5 ml/min. Columns were equilibrated in 50 mM phosphate buffer containing 0.3 M sodium chloride at pH 8.0. Strep-tagged Hv1a was eluted from columns using 2.5 mM desthiobiotin (in phosphate buffer; pH 8.0). For all other proteins supernatants were adjusted to 0.02 M sodium phosphate buffer, 0.4 M sodium chloride, pH 7.4 by adding 4× concentrated stock (4× Binding buffer [BB]). Recombinant pro-Hv1a Hv1a/GNA and pro-Hv1a/GNA were purified by nickel affinity chromatography on 5 ml HisTrap crude nickel columns (GE Healthcare) with a flow rate of 2 ml/min. After loading, the columns were washed with 1×BB (50 mM sodium phosphate; 0.4 M sodium chloride) and then with BB containing 0.025 M imidazole, and finally bound recombinant proteins were eluted with BB containing 0.2 M imidazole. In all cases eluted proteins were then checked for purity by SDS-PAGE, dialysed against deionised water using multiple changes to remove all small molecules, and freeze-dried. Concentrations of recombinant proteins were estimated by comparison to known amounts of GNA standards run on SDS-PAGE gels or by BCA analysis using a BCA™ Protein Assay Kit (Thermo Scientific).

Expression of PI1a and PI1a/GNA Fusion Proteins in Yeast pGAPZαB plasmids containing the PI1a and PI1a/GNA expression constructs were amplified in *E. coli*, purified and linearised with BlnI. Linearised plasmids were transformed into *Pichia pastoris* strain SMD1168H (Invitrogen) using the EasyComp Transformation kit (Invitrogen) as described in the manufacturer's protocol. Transformed yeast clones were plated and selected on YPG agar plates (1% yeast extract (w/v), 2% peptone (w/v), 4% glycerol (v/v), 1.5% agar (w/v)) containing zeocin (100 mg/ml). Selected clones (at least 10 for each construct) were checked for expression of recombinant proteins by analysis of culture supernatant from small-scale shake flask cultures grown for 2-3 days in YPG-zeocin media at 30° C. Samples of supernatant were separated by SDS-polyacrylamide gel electrophoresis; gels were blotted onto nitrocellulose and probed with anti-$(His)_6$ primary antibodies (BioRad) or anti-GNA primary antibodies, followed by washing, probing with HRP-conjugated secondary antibodies (BioRad), and detection of bound antibodies by ECL.

Selected clones of *P. pastoris* containing the integrated PI1a and PI1a/GNA constructs were grown in a 5 L Bio-Controlly ADI1010 bench-top fermenter (Applikon Biotechnology, Holland). For fermentation, two 100 ml YPG cultures of *P. pastoris* containing toxin or fusion genes were grown for 2-3 days at 30° C. with shaking, prior to being used to inoculate 2.5 L of sterile minimal media supplemented with PTM1 salts. Cultivation at 30° C., 30% dissolved oxygen, pH 4.5-5.0 with continuous agitation was continued with a ramped glycerol feed (5-10 ml/h) over a period of 4 days. Culture supernatant was separated from cells by centrifugation (20 min at 5000 g), and adjusted to 0.02 M sodium phosphate buffer, 0.4 M sodium chloride, pH 7.4 by adding 5× concentrated stock. Recombinant proteins were purified by nickel affinity chromatography on 5 ml HisTrap crude nickel columns (GE Healthcare) with a flow rate of 2 ml/min. After loading, the columns were washed with 0.02 M sodium phosphate buffer, 0.4 M sodium chloride pH 7.4 and the bound proteins were eluted with 0.2 M imidazole in the same buffer. Eluted proteins were checked for purity by SDS-PAGE, dialysed against deionised water using multiple changes to remove all small molecules, and freeze-dried. Concentrations of recombinant proteins were estimated by comparison to known amounts of GNA standards run on SDS-PAGE gels or by BCA analysis using a BCA™ Protein Assay Kit (Thermo Scientific).

Insect Bioassays $3^{rd}$-$5^{th}$ instar *Mamestra brassicae* larvae (approximately 30-55 mg in weight) were used for injection bioassays. Larvae were injected with varying doses of Hv1a, pro-Hv1a, pro-Hv1a/GNA, PI1a, Ao1bProPI1a, PI1a/GNA, Ao1bPro-PI1a/GNA, or Hv1aPro-PI1a/GNA (n=20 per dose) in 5 μl of PBS (phosphate buffered saline; 0.15 M NaCl, 0.015 M sodium-phosphate buffer, pH 7.2). Larvae for controls were injected with 5 μl 1×PBS. Paralysis and mortality was recorded 12-96 h after injection.

Droplet-feeding assays were carried out to assess the oral activity of Hv1a/GNA, pro-Hv1a/GNA, PI1a, Ao1bProPI1a, PI1a/GNA, Ao1bPro-PI1a/GNA, or Hv1aPro-PI1a/GNA towards third to fifth instar larvae of *M. brassicae*. Larvae were starved for approximately 24 h before feeding in order to encourage droplet consumption. Larvae were fed with a 2 μl droplet containing 20 μg of the above fusion proteins, 30 μg of toxins or 30 μg of GNA, in 1×PBS solution containing 10% sucrose (w/w). Control larvae were fed on PBS/sucrose droplets containing no added protein. Treated larvae were placed on standard artificial diet after consumption of the droplet.

The insecticidal effects of Hv1a/GNA and pro-Hv1a/GNA to *Acyrthosiphon pisum* (pea aphids) and *Sitobion avenae* (cereal aphids) was assayed by feeding 100 μl liquid artificial diet containing known concentrations of fusion proteins (Prosser and Douglas, 1992), using double parafilm sachets (diet droplet in the middle) to deliver diet to insects. The experiment used 1-2 day-old aphids and survival was assessed daily for six days.

Injection Bioassays: *Deroceras reticulatum* (Mollusc Grey Field Slug)

Hv1a/GNA and pro-Hv1a/GNA were tested for activity against adult slugs (*Deroceras reticulatum*) by injection into adult slugs (0.2-0.3 g). Slugs were chilled at 4° C. (for approximately 15 minutes) prior to injection of 25 μg, 50 μg or 100 μg of purified fusion proteins resuspended in 20 μl PBS. Mortality was assessed daily for 7 days.

Statistical Analysis

Survival data were analysed using Kaplan-Meier survival analysis, using Prism (v5) software. All other data analysis was carried out using Origin 8.5 graphing and data analysis software. ANOVA analysis (with Bonferroni-Dunn post-hoc tests) was carried out to determine any significant differences between treatments in the parameters measured.

Results

The present inventors have conducted experiments to investigate the effect of inclusion of a pro-region in an expression construct for a toxin on the biological activity of said toxin.

Experiments Investigating the Toxicity of Hv1a

Introduction

To investigate the effect of inclusion of a pro-region on the toxicity of recombinant toxins, ω-Hexatoxin-Hv1a was used. ω-Hexatoxin-Hv1a is a toxin isolated from the funnel-web spider *Hadroncyhe versuta*. ω-Hexatoxin-Hv1a (or ω-ACTX-Hv1a) is a calcium channel antagonist and it has previously been shown that ω-ACTX-Hv1a can block invertebrate but not vertebrate calcium channels.

Although it has been shown that ω-ACTX-Hv1a can be used on its own as a pesticide when applied topically to caterpillars (Khan et al., 2006), no further evidence for insecticidal activity of the peptide alone has been reported. In patent application PCT/GB2012/000287 the present inventors demonstrated that the toxicity of a recombinant toxin (ω-ACTX-Hv1a) expressed in *Pichia pastoris* could be enhanced by expressing the protein in fusion with the plant lectin GNA, which had previously been shown to cross the gut epithelium and deliver 'passenger' peptides from the gut to the circulatory system of invertebrate animals.

To further investigate how the potency of toxins expressed in vitro might be improved, the present inventors analysed the DNA sequences of the genes encoding arthropod toxins. The arthropod toxins utilised in PCT/GB2012/000287 are small, cysteine-rich proteins belonging to several superfamilies of protein sequences (which include toxins from organisms other than arthropods). The encoding genes include two sequences that are not present in the final protein product; a predicted N-terminal signal peptide that is removed during translation and a predicted pro-region, between the signal peptide and the final sequence of the protein as isolated (see FIG. 1A).

The present inventors investigated the effect of including the pro-region in the expression construct on the overall toxicity of the recombinant protein.

In the first instance, ω-ACTX-Hv1a was used, as this toxin contains a predicted pro-region in its gene sequence (see FIG. 1B).

Synthetic Gene Constructs, Expression and Purification of Recombinant Hv1a, Pro-Hv1a, Hv1a/GNA and Pro-Hv1a/GNA Recombinant Hv1a, pro-Hv1a, Hv1a/GNA and pro-Hv1a/GNA fusion protein constructs were synthesised based on the vector pGAPZαB, which possesses a strong constitutive promoter (GAPDH) to direct target gene expression. The pGAPZ vectors are integrating vectors in the expression host *Pichia pastoris* and selected transformants contain the expression construct integrated into the host genome. The constructs for expressing recombinant Hv1a and pro-Hv1a contained a predicted amino acid sequence corresponding to the published sequence for the toxin. For Hv1a, the mature peptide was cloned in frame with the yeast a-factor prepro-sequence and 8 amino acids encoding a Strep tag (i.e. WSHPQFEK (SEQ ID NO: 17) linked to the N-terminus of mature Hv1a sequence via a 3 amino acid linker 'GLQ'). For Pro-Hv1a, the N-terminal pro-region was arranged in-frame C-terminal to a sequence encoding the yeast a-factor prepro-sequence, and the construct also contained sequences encoding the myc epitope and $(His)_6$ tag, supplied by the vector, at the C-terminus of the predicted product. For Hv1a/GNA, the mature toxin sequence was fused to the N-terminus of a coding sequence corresponding to residues 1-105 of mature snowdrop lectin (GNA) via a 3 amino acid (AAA) linker peptide. For pro-Hv1a/GNA the synthetic pro-Hv1a coding sequence was fused to the N-terminus of a coding sequence corresponding to residues 1-105 of mature snowdrop lectin (GNA) via a 3 amino acid (AAA) linker peptide. Both fusion protein constructs were also arranged in-frame with the yeast α-factor prepro-sequence, and C-terminal to a sequence encoding $(His)_6$ tag, supplied by the vector. The constructs were assembled by ligation of endonuclease digested DNA and were checked by DNA sequencing after cloning.

Sequence verified clones, containing recombinant Hv1a, pro-Hv1a, Hv1a/GNA or pro-Hv1a/GNA were transformed into the *P. pastoris* protease-deficient strain SMD1168H and selected using the antibiotic zeocin. Selected clones were grown in shake flask cultures for 3-4 days at 30° C. and culture supernatants were analysed for the expression of recombinant proteins using western blotting. This enabled highly-expressing clones to be selected for production by bench-top fermentation. The majority of the analysed transformed yeast clones showed evidence of protein expression as judged by the presence of immunoreactive bands with the expected size on western blots (results not shown).

Fermentation of the selected clones was carried out in bioreactors under controlled environmental conditions. The use of the pGAP alpha factor secretory signal that directs the secretion of expressed proteins out of the cells and into the growth media, enabled subsequent purification of recombinant proteins from fermented culture supernatants. Supernatants were obtained by centrifugation, clarified by filtration and recombinant proteins were subsequently purified by affinity chromatography (Streptactin for Hv1a and nickel affinity for pro-Hv1a and pro-Hv1a/GNA). Eluted peaks containing target proteins were desalted by dialysis and lyophilised. For yields of recombinant proteins, Hv1a was produced at approximately 5-10 mg/L culture supernatant; pro-Hv1a was produced at approximately 40 mg/L, as estimated by BCA quantification and Hv1a/GNA at approximately 40 mg/L and pro-Hv1a/GNA at approximately 21 mg/L, as estimated by semi-quantitative SDS-PAGE.

Figures 2A, 2B, 2C:
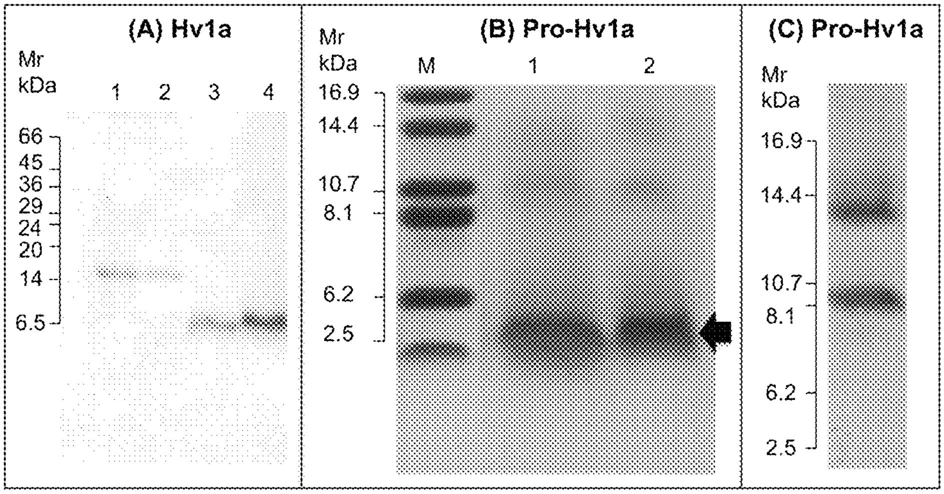

As shown in FIG. 2A (lanes 3 and 4), 5' Strep tagged mature purified Hv1a separated on SDS-PAGE gels as a single protein of approximately 6.5 kDa, comparable to the predicted molecular mass of 5.47 kDa (gels were not optimised for the separation of low molecular weight proteins). Purified recombinant pro-Hv1a was separated using Tris-Tricine SDS-PAGE gels and analysed by both staining for total protein and western blotting using anti-His antibodies (FIGS. 2B & C). The recombinant toxin pro-Hv1a gave a major protein band at approximately 4 kDa and further weaker bands in molecular mass range 6-16 kDa on Tris-Tricine gels. The dominant band of approximately 4 kDa is not immunoreactive with anti-$(His)_6$ antibodies (FIG. 2C) and the molecular mass is consistent with the predicted mass (4.06 kDa) following cleavage of the C-terminal tag region. Pull down of non-His tagged proteins along with His-tagged proteins from nickel affinity columns has previously been observed for other recombinant proteins recovered from *Pichia* supernatants. The 10 kDa protein that shows positive immunoreactivity with anti-$(His)_6$ antibodies corresponds to the predicted mass (9 kDa) for recombinant Hv1a including the pro-region, suggesting that cleavage of the pro-region is incomplete during processing by yeast cells. The 14 kDa band also immunoreactive with anti-$(His)_6$ antibodies may represent a dimeric form of Hv1a given that the predicted mass of Hv1a containing the C-terminal His region but no pro-region is 6.74 kDa.

Lyophilised samples of purified pro-Hv1a/GNA, Hv1a/GNA and MODHv1a/GNA were analysed on SDS-PAGE gels (FIG. 3). Two bands of approximately 19 kDa and 14 kDa were observed for all fusion proteins. The predicted molecular mass for Hv1a/GNA is 16.27 kDa, and for pro-Hv1a/GNA without the pro-region but containing a $(His)_6$ tag is 16.95, both slightly less than the observed 19 kDa band. However, the identical separation of pro-Hv1a/GNA and Hv1a/GNA on SDS-PAGE gels suggests that the pro-region has been cleaved from pro-Hv1a/GNA during processing by *P. pastoris* cells. The predicted mass for intact MODHv1a/GNA is 17.09 kDa and correspondingly this protein runs as a slightly larger protein as compared to Hv1a/GNA and pro-Hv1a/GNA due to the presence of an additional histidine tag that is not present in Hv1a/GNA. In all cases the smaller 14 kDa band is immunoreactive with GNA antibodies (results not shown) and corresponds in size to GNA from which the Hv1a toxin has been cleaved. As observed previously for Hv1a/GNA (Fitches et al., 2012), the ratio of intact pro-Hv1a/GNA fusion protein to cleaved GNA was estimated as approx. 1:1 as judged by Coomassie blue staining on SDS-PAGE gels, whereas modification of the Hv1a sequence in MODHv1a/GNA results in a higher recovery of intact fusion protein (ratio intact:cleaved 2:1). Quantification of the Hv1a/GNA fusion proteins was based on comparative band intensity with GNA standards of known concentration as shown in FIG. 3.

Injection Toxicity of Recombinant Hv1a, Pro-Hv1a, Hv1a/GNA and Pro-Hv1a/GNA Fusion Protein to Cabbage Moth (*Mamestra brassicae*) Larvae Injections of Hv1a at doses of up to 100 μg of the recombinant toxin did not result in any larval mortality with survival comparable to controls (n=40; survival >90%). This demonstrated that the expression of mature Hv1a peptide without an N-terminal pro-region resulted in the production of biologically inactive toxin, suggesting that the toxin was incorrectly processed and/or folded during synthesis by yeast cells. By contrast, injections of newly eclosed $3^{rd}$-$4^{th}$ (~30-40 mg) and $5^{th}$ instar (~45-55 mg) *M. brassicae* larvae with either pro-Hv1a, Hv1a/GNA, MODHv1a/GNA or pro-Hv1a/GNA led to significant larval mortality.

Figures 4A, 4B, 4C:
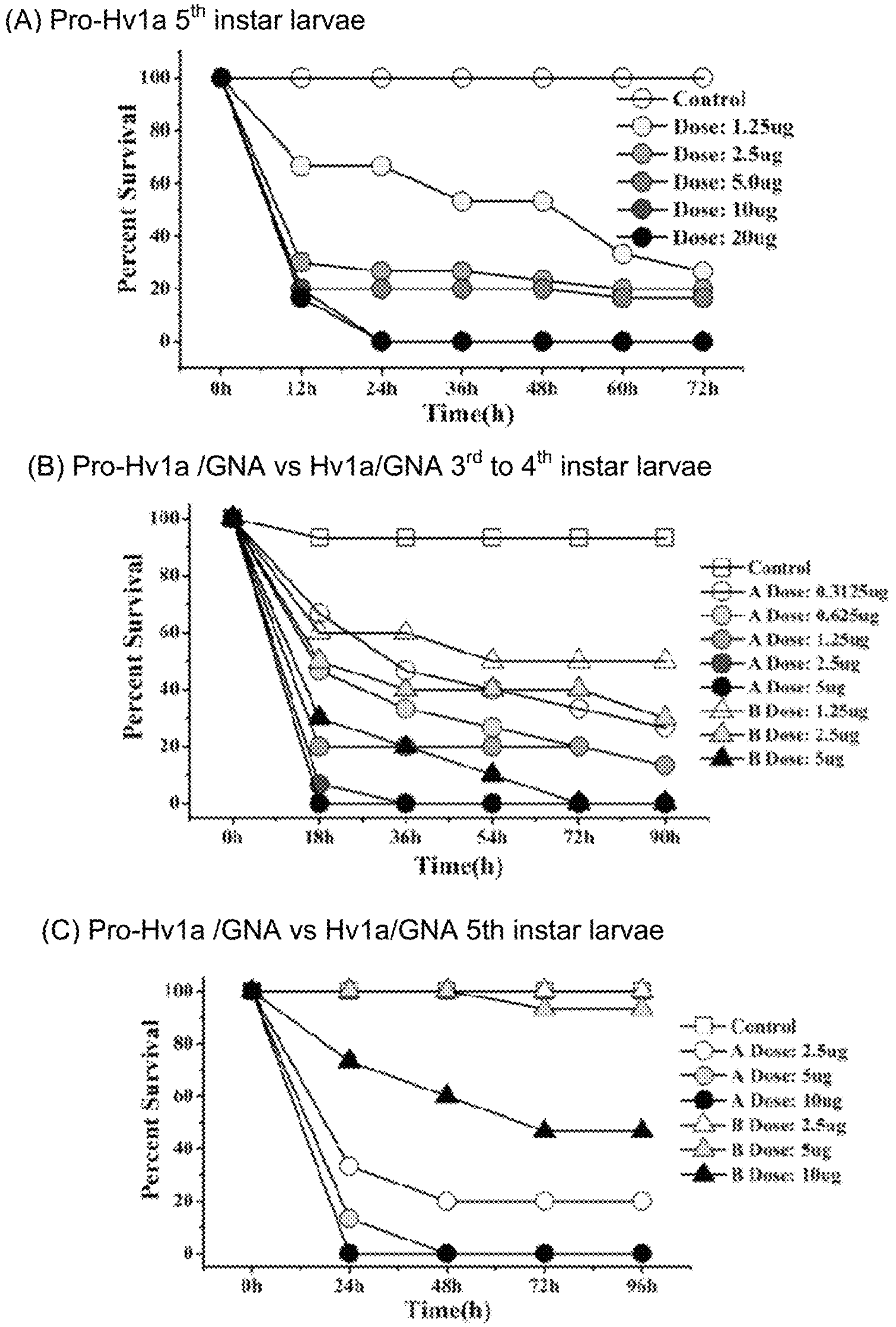

As shown in FIG. 4A the effects of recombinant pro-Hv1a after injection into $5^{th}$ instar larvae were dose dependent. Injection doses of 10 μg and 20 μg pro-Hv1a/insect resulted in complete mortality 24 hours post injection and injection of 5 μg/insect resulted in 80% mortality 24 hours after injection. At the lowest dose of 1.25 μg/insect, all insects displayed flaccid paralysis and a temporary absence of feeding although some paralysed insects recovered and were able to resume feeding 2-3 hours after injection. From these assays, the estimated $LD_{50}$ (lethal dose; 48 hours) for the recombinant pro-Hv1a was 25 μg/g insect. As summarised in Table 1 this is approximately 3-fold lower than that previously published for recombinant Hv1a toxin produced in *E. coli*, whose $LD_{50}$ (72 hours) was ~69 μg/g insect.

As shown in FIGS. 4B & C injections of 3-$4^{th}$ and $5^{th}$ instar *M. brassicae* larvae with pro-Hv1a/GNA demonstrated increased toxicity as compared to Hv1a/GNA. For example injections of 10 μg Hv1a/GNA into $5^{th}$ instar larvae resulted in 50% mortality after 72 hours as compared to 100% mortality recorded 24 hours after injection of the same dose of pro-Hv1a/GNA. Significant larval mortality (75%) was observed at a pro-Hv1a/GNA dose of 2.5 μg/insect whereas injections of 5 or 10 μg Hv1a/GNA did not result in any significant levels of mortality for $5^{th}$ instar larvae. Similar results were observed following the injection of smaller 3-$4^{th}$ instar larvae (FIG. 4B). As shown in Table 1 $LD_{50}$ values estimated for pro-Hv1a/GNA were some 10-fold lower (4.6 μg/g insect) as compared to an $LD_{50}$ of 55 μg/g insect for Hv1a/GNA. This demonstrates that the addition of the pro-region to the Hv1a/GNA construct results in the production of fusion protein that is significantly more toxic as compared to protein derived from a construct encoding the mature toxin sequence fused to GNA. More surprisingly, the $LD_{50}$ value of 4.6 μg/g insect calculated for pro-Hv1a/GNA is some 5-fold lower than 25 μg/g insect estimated for pro-Hv1a. This shows that linkage of the pro-Hv1a to GNA results in a protein with higher biological activity than either pro-Hv1a alone, or Hv1a/GNA without the pro-region. The $LD_{50}$ value of 4.6 μg/g insect calculated for pro-Hv1a/GNA is also over 2-fold lower than the literature value for native Hv1a (as opposed to recombinant Hv1a; see table 1). This literature value represents the $LD_{50}$ value in *Heliothis*, a species of the same insect order as *M. brassicae*. We hypothesise that fusing GNA to pro-Hv1a further acts to facilitate correct processing and folding of the Hv1a toxin by *P. pastoris* cells, allowing for further increases in biological activity to be attained. Injections of GNA alone at up to 40 μg/insect do not result in mortality of *M. brassicae* larvae.

TABLE 1

Toxicity of recombinant toxins and fusion proteins in injection bioassays with *Mamestra brassicae* larvae

| | Hv1a (literature) | Hv1a | Pro-Hv1a | Hv1a/GNA | Pro-Hv1a/GNA | Hv1a (*E. coli*) |
|---|---|---|---|---|---|---|
| $LD_{50}$ | 12 μg/g (*Heliothis* sp.)* | >1000 μg/g | 25 μg/g (48 h) <25 μg/g (72 h) | 55 μg/g (72 h) | 4.6 μg/g (48 h) | 69 μg/g (72 h) |

*Data not available for *M. brassicae*

Ingestion Toxicity of Recombinant Hv1a, Pro-Hv1a and Pro-Hv1a/GNA Fusion Protein to Cabbage Moth (*M. brassicae*) Larvae The oral activity of proHv1a/GNA and Hv1a/GNA was assessed by feeding 2 μl droplets containing 20 μg of fusion protein to newly eclosed third instar *M. brassicae* larvae. Control treatments were 20 μg of either GNA or pro-Hv1a, in addition to a no-added protein control group. As shown in FIG. 5 and Table 2, significant effects were observed only for larvae fed on pro-Hv1a/GNA, with 90% mortality recorded 5 days after the ingestion of a single droplet of fusion protein. By contrast, mortality was only 30% for the Hv1a/GNA fusion protein, only slightly greater than the 20% and 15% mortality observed for GNA and pro-Hv1a treatments, respectively. Similar results were observed in assays where a single dose of 20 μg of pro-Hv1a/GNA fusion protein was found to cause 30% mortality of fifth instar larvae over 4 days, whereas no mortality was observed for larvae fed on either 20 μg of Hv1a/GNA, or pro-Hv1a (results not shown).

TABLE 2

| Toxicity of recombinant toxins and fusion proteins in oral feeding assays with *Mamestra brassicae* larvae | | | | |
|---|---|---|---|---|
| | Pro-Hv1a | Hv1a/GNA | Pro-Hv1a/GNA | Hv1a (*E. coli*) |
| Percentage Survival | 85% (5 d) 600 μg/g | 70% (5 d) 500 μg/g | 10% (5 d) 500 μg/g | 100% (5 d) 180 μg/g |

Figure 6A:
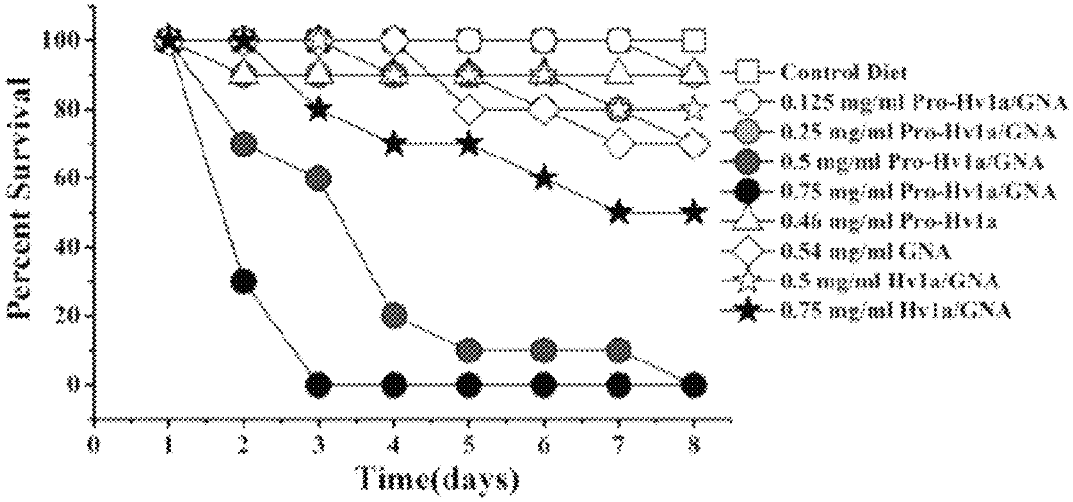

Ingestion Toxicity of Recombinant Hv1a, Pro-Hv1a and Pro-Hv1a/GNA Fusion Protein to Pea (*A. pisum*) and Cereal (*Sitobion avenae*) Aphids Recombinant pro-Hv1a protein, pro-Hv1a/GNA and Hv1a/GNA were tested for oral activity against pea and cereal aphids by incorporation into artificial diet at concentrations of 0.125 mg-0.75 mg/ml (125-750 ppm). As observed for lepidopteran larvae, purified pro-Hv1a/GNA was found to be significantly more toxic than Hv1a/GNA to both aphid species (FIGS. 6A & B). Pro-Hv1a/GNA at 750 ppm caused 100% mortality of pea aphids after 3 days, whereas the same dose of Hv1a/GNA resulted in only 50% mortality after 8 days of feeding. At a lower dose of 500 ppm, mortality after 8 days of feeding was 100% for pea aphids fed on pro-Hv1a/GNA as compared to 20% for Hv1a/GNA.

Figure 6B:
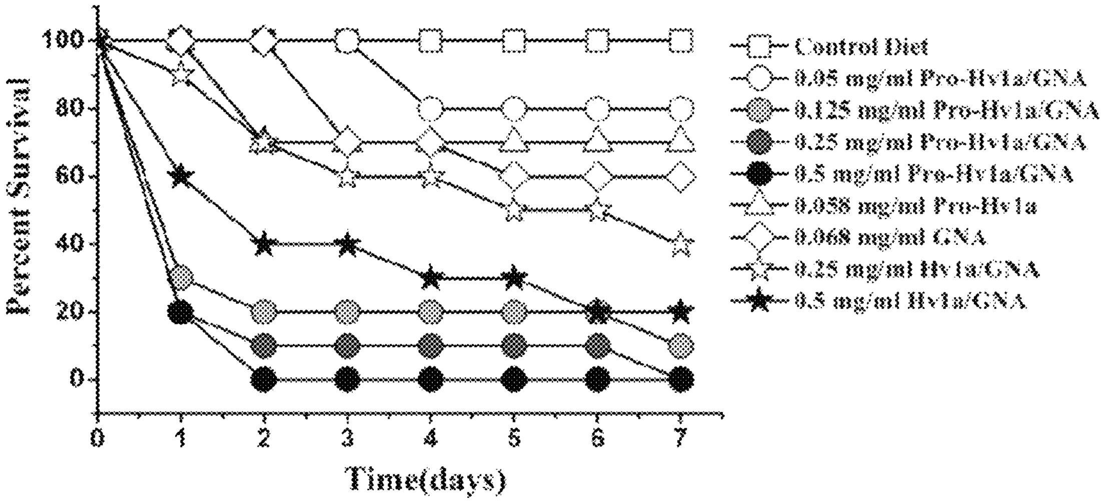

Pro-Hv1a/GNA was also found to be significantly more toxic than Hv1a/GNA to cereal aphids. As shown in FIG. 6B, 100% mortality was recorded for cereal aphids fed on diets containing 250 ppm of pro-Hv1a/GNA for 7 days as compared to 60% for Hv1a/GNA fed aphids. Cereal aphids appear to be more susceptible to pro-Hv1a/GNA than pea aphids as significant levels of mortality were observed at levels as low as 125 ppm pro-Hv1a/GNA (80% mortality after 2 days of feeding) whereas no mortality was recorded for pea aphids fed on the same dose of fusion protein.

Injection Toxicity of Recombinant MODHv1a and Pro-Hv1a/GNA Fusion Protein to Grey Field Slugs (*Deroceras reticulatum*)

MODHv1a/GNA and Pro-Hv1a/GNA were tested for activity against slugs (*D. reticulatum*) by injection into adult slugs (~0.2 g). MODHv1a/GNA corresponds to the modified form of Hv1a/GNA, where a single amino acid change at the C-terminus of Hv1a has been shown to improve expression of intact fusion protein but has equivalent toxicity to Hv1a/GNA. Slugs were chilled at 4° C. (for ~15 minutes) prior to injection of 25, 50 or 100 μg of purified Hv1a/GNA resuspended in 20 μl PBS. Mortality was assessed daily for 7 days. FIG. 7 shows dose dependent mortality observed for both treatments. Mortality was significantly greater for pro-Hv1a/GNA as compared to MODHv1a/GNA for all doses injected ($P<0.05$; Mantel Cox tests). For example, 100% mortality was recorded 3 days after injection of 50 μg of pro-Hv1a/GNA as compared to 10% mortality observed 5 days after injection of 50 μg of MODHv1a/GNA.

Experiments Investigating the Toxicity of PI1a

Introduction

Results obtained for the Hva1/GNA fusion protein were extended by taking a toxin protein whose gene sequence did not include a predicted pro-region and incorporating a pro-region into the expression construct based on similar sequences in the global protein database. The toxin δ-amaurobitoxin-PI1a from the spider *Pireneitega luctuosa* was utilised.

Expression and Purification of Recombinant PI1a and PI1a/GNA

Expression constructs for the production of recombinant proteins in *Pichia pastoris* were based on the vector pGAPZαB, which contains a strong constitutive promoter used to direct expression of the recombinant protein and which is designed to integrate into the host genome at the GAPDH locus, giving stable transformants. Expression constructs for the production of recombinant PI1a contained a synthetic coding sequence corresponding to the published amino acid sequence for the toxin designated PI1a, arranged in-frame C-terminal to a sequence encoding the yeast α-factor prepro-sequence. Constructs containing toxin pro-regions had these inserted between the yeast α-factor prepro-sequence and the PI1a toxin sequence. The pro-regions used were taken from the closely related toxin U3-agatoxin-Ao1b from the spider *Agelena orientalis* (a cDNA sequence including the pro-region is not available for PI1a), designated Ao1bPro-PI1a, and from the pro-region for the Hv1a atracotoxin, as previously described, designated Hv1aPro-PI1a. The expression constructs also contained C-terminal sequences encoding the myc epitope and $(His)_6$ tag, supplied by the vector.

Three expression constructs were created for the production of recombinant PI1a/GNA fusion protein and all contained the mature PI1a coding sequence fused to the N-terminus of a coding sequence corresponding to residues 1-105 of mature snowdrop lectin (GNA) via a 3 amino acid linker peptide; again, the fusion proteins were arranged in-frame C-terminal to the α-factor prepro-sequence, and N-terminal to a sequence encoding the $(His)_6$ tag, supplied by the vector. Modified fusion protein constructs also contained the pro-regions of Ao1b and Hv1a as described above, inserted between the yeast α-factor prepro-sequence and the mature coding sequence of PI1a; they were designated Ao1bPro-PI1a/GNA and Hv1aPro-PI1a/GNA. The constructs were assembled by restriction-ligation and were checked by DNA sequencing after cloning.

Verified clones of expression constructs were transformed into the protease-deficient *P. pastoris* strain SMD1168H, using antibiotic (zeocin) selection for transformants. Approximately 50 resistant colonies were obtained for each expression construct. Culture supernatant from selected clones grown in shake-flask cultures was analysed for production of recombinant proteins by western blotting, to allow selection of clones producing the highest levels of PI1a and PI1a/GNA fusion proteins. Screening of large numbers of transformed yeast clones was not necessary, since most clones were expressing recombinant proteins, as judged by the presence of immunoreactive bands of the expected size on western blots of culture supernatants (results not shown).

For each construct, the best-expressing clone of those screened in small-scale cultures was selected for large-scale protein production by bench top fermentation. Culture supernatants were purified by nickel affinity chromatography and eluted peaks were desalted by dialysis and lyophilized. Yields of recombinant proteins were comparable to other fusion proteins prior to optimisation; PI1a was produced at approximately 26 mg/L, Ao1bPro-PI1a at approximately 32 mg/L, PI1a/GNA at approximately 21 mg/L, Ao1bPro-PI1a/GNA at approximately 32 mg/L and Hv1aPro-PI1a at approximately 13 mg/L as estimated by semi-quantitative analysis.

Figures 8A, 8B, 8C, 8D:
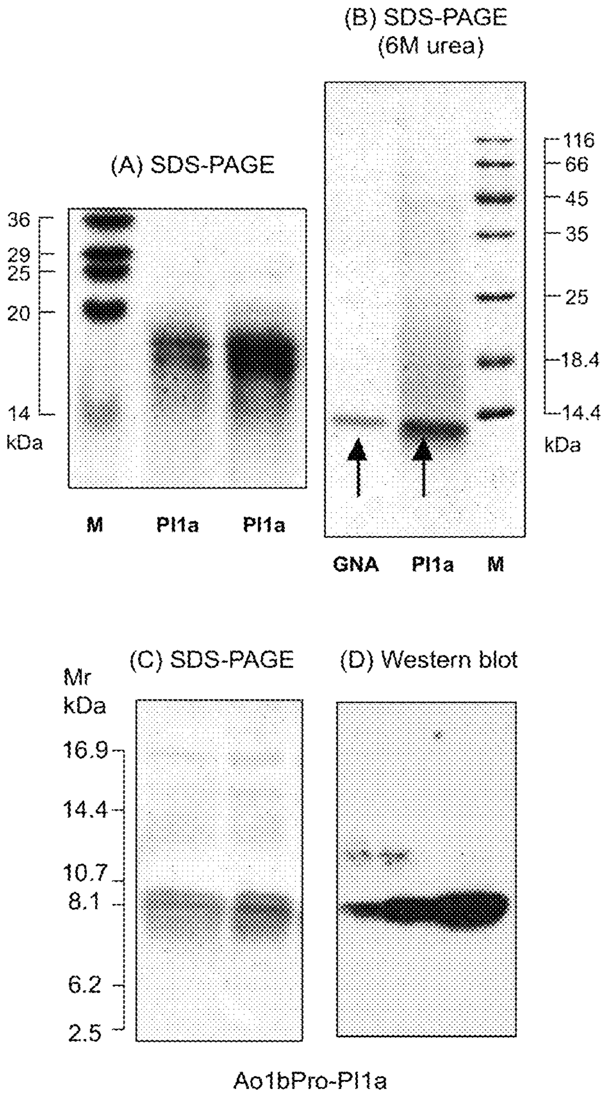

Purified recombinant PI1a toxins were analysed by SDS-PAGE and western blotting (FIG. 8). The recombinant toxin PI1a produced by the construct without the added pro-region ran as a closely spaced double band at an indicated molecular weight of approximately 18 kDa on SDS-PAGE gels (FIG. 8A); both bands were immunoreactive with anti-$(His)_6$ antibodies. The predicted molecular weight of recombinant PI1a, including the tag sequences is 6.87 kDa. The double band of toxin was reproducible with different gels, samples and use of reducing agents prior to electrophoresis, but was considered to be an artefact of the gel system, possibly as a result of poor binding of SDS to the polypeptide. When the same samples were pre-treated with 6 M urea, PI1a gave a single band at an indicated molecular weight of 14 kDa (FIG. 8B); the shift in mobility is indicative of gel artefacts, and the single band indicates homogeneity of the product. Further analysis on urea-containing gels gave single bands for PI1a, with indicated molecular weights of ~11 kDa without blocking cysteine residues and ~9 kDa after treatment with iodoacetamide to block cysteine residues; these results are diagnostic of incorrect molecular weights under "normal" conditions due to residual secondary structure and interactions between cysteine residues prior to or during electrophoresis. N-terminal sequencing verified incomplete processing of the Kex2 pGAPZαB cleavage site resulting in an additional glutamic acid and alanine residue at the N-terminus and a predicted product mass of 7.07 kDa. Interestingly, PI1a produced by the modified construct incorporating the pro-region (Ao1bPro-PI1a) ran as a closely spaced double band at ~9 kDa under "normal" SDS-PAGE conditions, with some evidence of a diffuse band at higher molecular weight (FIG. 8C). The predicted molecular mass of the peptide including the additional pro-region is 8.6 kDa. N-terminal sequencing confirmed that the pro-region was present in the protein product and that cleavage had occurred between alanine and the primary residue of the Ao1b pro-region isoleucine giving a predicted molecular mass of 8.46 kDa.

Figures 9A, 9B, 9C, 9D:
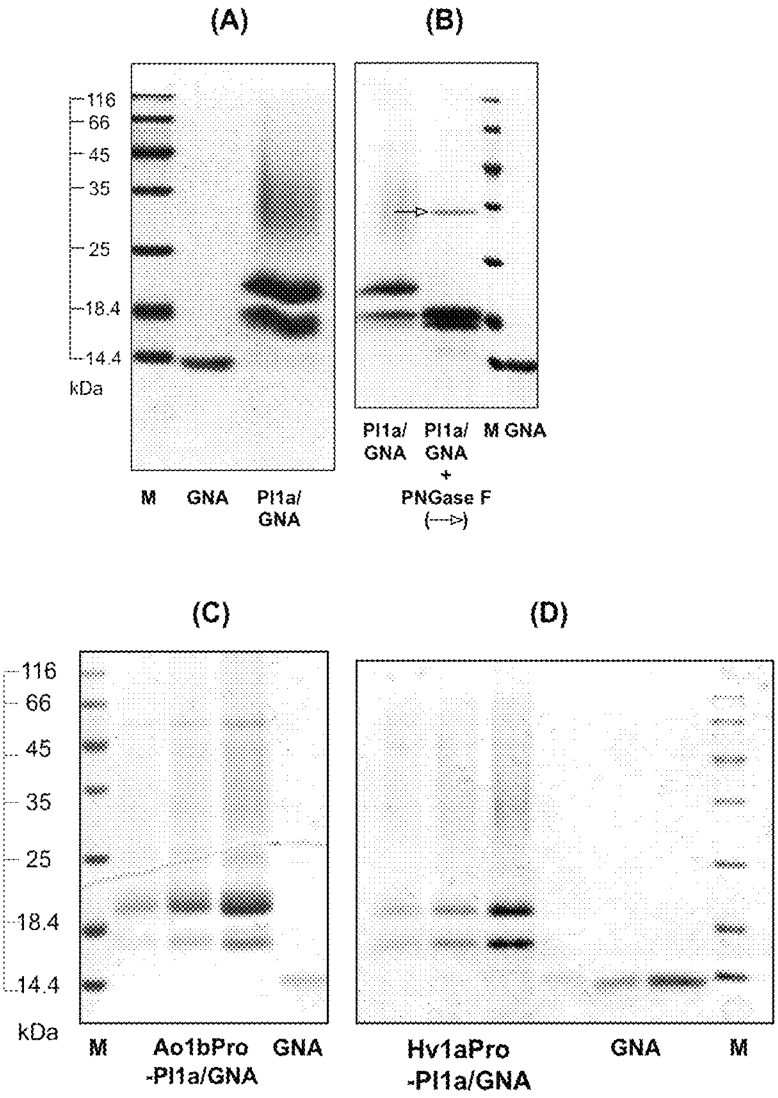

The "normal" PI1a/GNA fusion protein (i.e. derived from a construct that did not contain an additional pro-region) separated on SDS-PAGE gels as two major proteins of indicated sizes of 18 and 21 kDa (FIG. 9A). The 18 kDa protein, immunoreactive with anti-GNA antibodies (results not shown) corresponded in mass to that predicted for recombinant PI1a/GNA (17.1 kDa). The 21 kDa protein was also immunoreactive with anti-GNA antibodies, and had an identical N-terminal sequence to the 18 kDa band. Treatment with the deglycosylating enzyme PNGase F, which cleaves carbohydrate side chains attached to Asn residues through N-glycosidic bonds, removed this band, while the intensity of the "correct" band for the PI1a/GNA fusion protein increased as a result of the treatment (FIG. 9B). This result suggests that the extra band is due to "core" glycosylation of the fusion protein by *P. pastoris* during synthesis and secretion. GNA contains no potential N-glycosylation sites, but the PI1a toxin sequence contains a potential N-glycosylation site (N-X-S/T) at Asn-35. The N-terminal sequence of the single band was determined as E-A-A-A-G-(SEQ ID NO: 18), as expected for the fusion protein after removal of the yeast α-factor prepro-region during translation and secretion from *P. pastoris*. In addition a small amount of a band at an indicated molecular weight similar to recombinant GNA (12.7 kDa), which was immunoreactive to anti-GNA antibodies (results not shown), suggesting a small amount of cleavage of the fusion protein into its components was occurring during production and purification. The ratio of intact PI1a/GNA fusion protein to cleaved GNA was estimated as ~30:1 as judged by Coomassie blue staining on SDS-PAGE gels.

Both of the PI1a/GNA fusion proteins derived from constructs containing additional pro-region sequences (i.e. Ao1bPro-PI1a/GNA and Hv1aPro-PI1a/GNA) separated on SDS-PAGE gels as two major staining bands of approximately 17 and 21 kDa (FIGS. 9C & D). The smaller 17 kDa protein corresponds in mass to that predicted for Ao1bPro-PI1a/GNA and Hv1aPro-PI1a/GNA (16.94 kDa) following removal of the pro-region, suggesting that in both cases the pro-region is removed during processing by yeast cells. The larger 21 kDa protein band is most likely to represent glycosylated protein, as was observed for PI1a/GNA. Ao1bPro-PI1a/GNA and Hv1aPro-PI1a/GNA both expressed as 100% intact fusion protein with no evidence by SDS-PAGE and western blotting for cleavage between the toxin and GNA sequences.

Figure 10A:
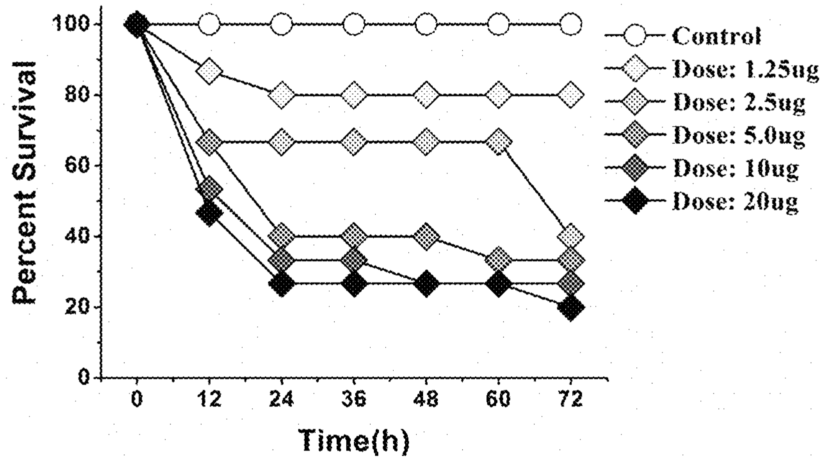
Figure 10B:
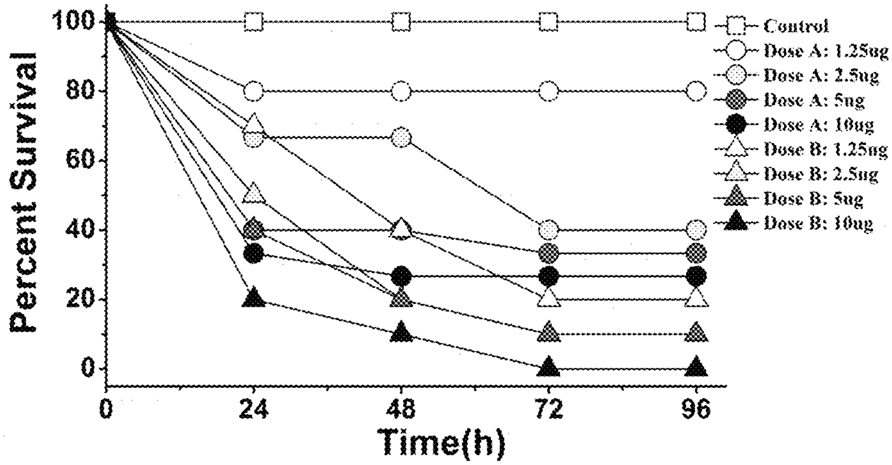

Injection Toxicity of Recombinant PI1a and Ao1bPro-PI1a Protein to Cabbage Moth (*M. brassicae*) Larvae Newly eclosed $5^{th}$ instar larvae (~45-55 mg in weight) of *M. brassicae* were injected with purified recombinant proteins to assess and compare in vivo activity of the toxins and fusion proteins. FIG. 10A shows survival of larvae following injection with PI1a and FIG. 10B shows survival following injection of comparable doses of PI1a and Ao1bPro-PI1a. Larvae injected with PI1a toxin all displayed flaccid paralysis within 1-2 hours (little mobility and almost a complete absence of feeding). Most mortality was observed within the first 24 hours. After a period of paralysis, some insects showed progressive recovery and were able to recommence feeding. The effects of PI1a were dose dependent, with mortality after 24 hours ranging from 75% at 20 μg toxin/insect to 20% at 1.25 μg toxin/insect. Even at high doses of toxin, complete mortality after 72 hours was not observed. From these assays, the estimated $LD_{50}$ (48 hours) for the recombinant PI1a was 4.1 μg/insect or 82 μg/g insect, based on an average larval weight of 50 mg (see Table 3). The literature $LD_{50}$ value for native PI1a (as opposed to recombinant PI1a) is 9.5 μg/g. This literature value represents the $LD_{50}$ value in *Spodoptera*, a species of the same insect order as *M. brassicae*.

Recombinant PI1a produced from the modified expression construct, including the pro-region from U3-agatoxin-Ao1b, showed similar toxic effects to PI1a, but was consistently more effective at lower doses than PI1a produced from the construct without this additional sequence (FIG. 10B). Again, the major effects of Ao1bPro-PI1a on mortality were observed during the first 24 hours, with mortality ranging from 80% at 10 μg toxin/insect to 30% at 1.25 μg toxin/insect. In these assays, there was a trend for mortality caused by toxin produced by the modified construct to continue to increase to 72 hours and the highest dose of toxin (10 μg toxin/insect) caused 100% mortality at 72 hours. Assays carried out at the same time with PI1a produced by the unmodified construct gave similar results to the previous assay and direct comparison between the two samples in the same assay showed that differences between PI1a produced by the unmodified and modified constructs were statistically significant when identical dose survival curves were analysed (FIG. 10B). The estimated $LD_{50}$ (48 hours) for recombinant PI1a produced from the modified construct (Ao1bPro-PI1a) was ~1.0 μg/insect, or 21 μg/g insect based on a mean larval weight of 50 mg; this is equivalent to an increase in toxicity of μ4-fold (see Table 3).

TABLE 3

Toxicity of recombinant toxins and fusion proteins in injection bioassays with *Mamestra brassicae* larvae

| | PI1a (literature) | PI1a | Ao1bPro-PI1a | PI1a/GNA | Ao1bPro-PI1a/GNA | Hv1aPro-PI1a/GNA |
|---|---|---|---|---|---|---|
| $LD_{50}$ | 9.5 μg/g (*Spodoptera* sp.)* | 82 μg/g | 21 μg/g | 11 μg/g (28 μg/g fusion) | 7.6 μg/g (19 μg/g fusion ) | <5 μg/g (<12 μg/g fusion) |

*data not available for *M. brassicae*

Figures 11A, 11B, 11C:
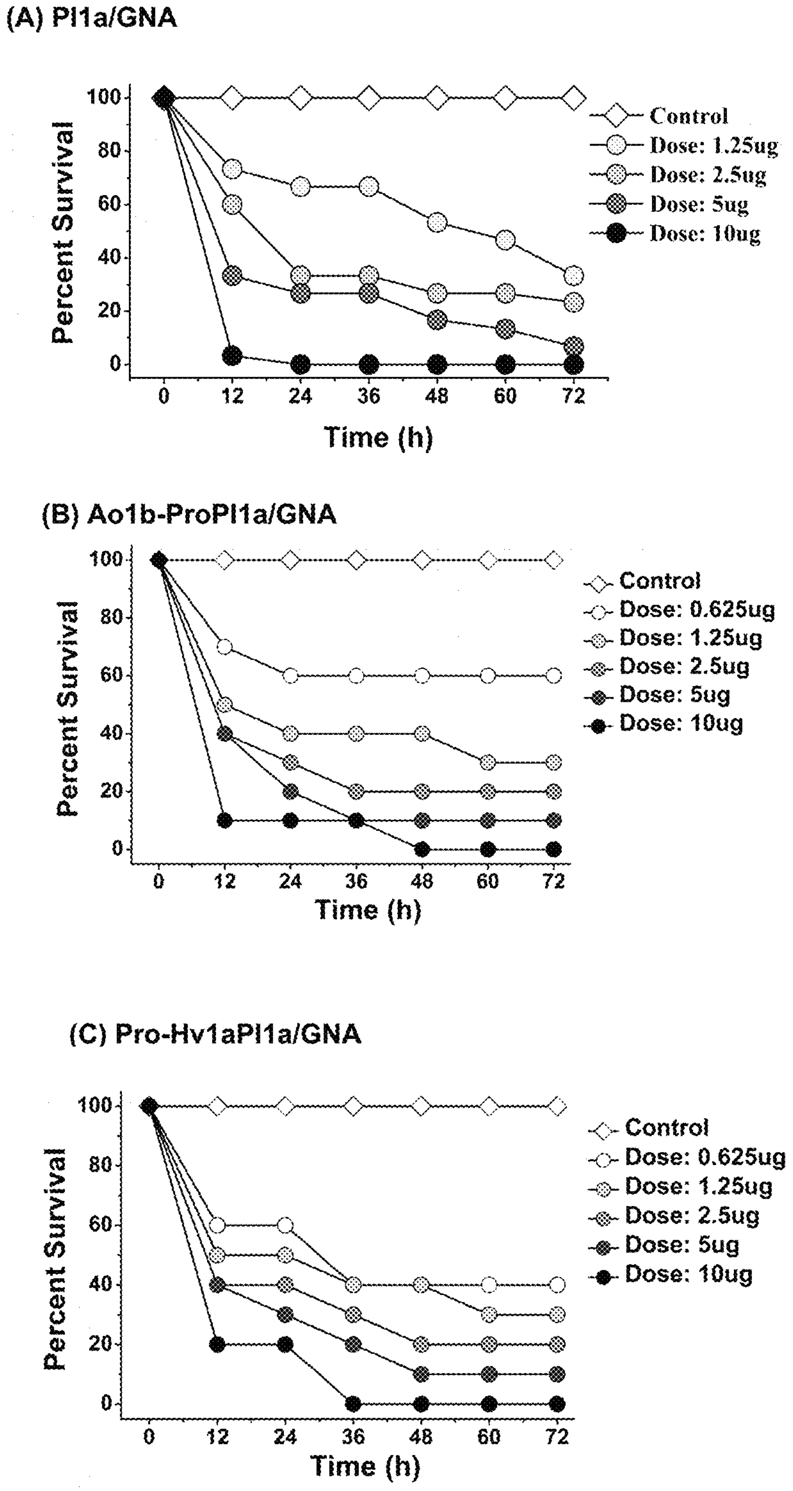

The PI1a/GNA fusion protein also caused paralysis and mortality when injected into *M. brassicae* larvae and was significantly more effective than toxin alone (FIG. 11A). When larvae were injected with 1.25-10 μg fusion protein/insect (equivalent to 0.50-4.0 μg PI1a/insect, since the molecular weight of recombinant PI1a is ~0.404 of that of the PI1a/GNA fusion protein), significant mortality was observed at all doses, and complete mortality after 24 hours was observed at the highest dose (FIG. 11A). As with PI1a, most mortality was observed within the first 24 hours of the assay and effects were dose dependent, ranging from 100% mortality at 10 μg fusion protein/insect to 35% mortality at 1.25 μg fusion protein/insect. Mortality at this lowest dose of fusion protein increased to 65% after 72 h whereas mortality from injection of 1.25 μg toxin alone did not change from 20% between 24 and 72 hours. From these assays, the estimated $LD_{50}$ (48 hours) for the recombinant PI1a/GNA fusion protein was 1.4 μg/insect, or 28 μg/g insect, based on a mean larval weight of 50 mg. The $LD_{50}$ is equivalent to 0.56 μg PI1a toxin per insect, making the PI1a/GNA fusion protein ~7 times as active as the toxin produced by the unmodified construct, and ~2 times as active as the toxin produced by the modified Ao1b-Pro-PI1a construct, on a molar basis. A similar ratio is obtained by using mortality figures at 72 hours. Direct comparisons of mortality produced by identical doses of toxin and fusion proteins show that the three treatments are different from each other, and from control, at $p<0.0001$ (ANOVA). In all these assays, no mortality of control-injected insects was observed over 72 hours.

As observed with PI1a toxin, addition of the Ao1b pro-region to the PI1a/GNA fusion protein expression construct resulted in a protein product with enhanced biological activity (FIG. 11B). The fusion protein product derived from this construct had an estimated $LD_{50}$ (48 hours) of 0.94 μg/insect, with increased mortalities at all doses except the highest. Addition of an alternative pro-region from the pro-HV1a toxin, to the PI1a/GNA expression construct also enhanced the biological activity of the resulting fusion protein (FIG. 11C); this protein had an estimated $LD_{50}$ (48 hours) of <0.6 μg/insect, although overall mortality values were similar to the pro-Ao1b-PI1a/GNA fusion protein. These data suggest that a two-fold increase in toxicity can be obtained by including pro-regions in the expression constructs for P1a/GNA.

Ingestion Toxicity of Recombinant PI1a/GNA, Ao1bPro-PI1a/GNA and Pro-HvlaPI1a/GNA Proteins to Cabbage Moth (*M. brassicae*) Larvae A similar increase in toxicity of fusion proteins derived from expression constructs including pro-regions to that observed in injection assays was also observed in droplet feeding assays with 3rd stadium *M. brassicae* larvae (FIG. 12). Following ingestion of a single 2 μl droplet containing 20 μg of fusion protein, mortality after 5 days was 40% for PI1a/GNA; 50% for Ao1bPro-PI1a/GNA and 70% for Hv1aPro-PI1a/GNA (data summarised in Table 4). Minimal reductions in survival (0-20%) were observed for control treatments where larvae were fed on 30 μg toxin or GNA and survival curves for controls were significantly different to fusion protein treatments. This provides further evidence that the addition of pro-regions to the PI1a/GNA construct results in increased biological activity. As for injection studies the use of the Hv1a pro-region was seen to result in the greatest enhancement of toxicity over the non-modified PI1a/GNA fusion protein.

TABLE 4

Toxicity of recombinant toxins and fusion proteins in oral feeding assays with *Mamestra brassicae* larvae

| | PI1a (recombinant) | Ao1bPro-Hv1a | PI1a/GNA | Ao1bPro-PI1a/GNA | Hv1aPro-PI1a/GNA |
|---|---|---|---|---|---|
| Percentage Survival | 90% (5 d) 400 μg/g | 80% (5 d) 400 μg/g | 60% (5 d) 500 μg/g | 50% (5 d) 500 μg/g | 30% (5 d) 500 μg/g |

REFERENCES

Becker & Guarente High-efficiency transformation of yeast by electroporation. *Methods Enzymol.* (1991) 194:182-187.

Berent S. L., Mahmoudi M., Torczynscki R. M., Bragg P. W., Bollon A. P. Comparison of oligonucleotide and long DNA fragments as probes in DNA and RNA dot, southern, northern, colony and plaque hybridizations. Biotechniques. (1985) 3:208-220

Douglas, A. E. and Prosser, W. A. Synthesis of the essential amino acid tryptophan in the pea aphid (*Acyrthosiphon pisum*) symbiosis. Journal of Insect Physiology (1992) 38: 565-568.

Fitches, E. C., Pyati, P., King, G. F. and Gatehouse, J. A. Fusion to snowdrop lectin magnifies the oral activity of insecticidal ω-Hexatoxin-Hv1a peptide by enabling its delivery to the central nervous system. PLoS One (2012) 7:e39389

Fitches, E., Woodhouse S. D. Edwards, J. P., Gatehouse, J. A. In vitro and in vivo binding of snowdrop (*Galanthus nivalis* agglutinin; GNA) and jackbean (*Canavalia ensiformis*; Con A) lectins within tomato moth (*Lacanobia oleracea*) larvae; mechanisms of insecticidal action. Journal of Insect Physiology (2001) 47:777-787.

Fletcher J. I., Smith R., O'Donoghue S. I., Nilges M., Connor M., Howden M. E. H., Christie M. J., King G. F. The structure of a novel insecticidal neurotoxin, omega-atracotoxin-HV1, from the venom of an Australian funnel web spider. Nature Structural Biology (1997) 4:559-566.

Kaas, Q., Westermann, J. C. and Craik, D. J. Conopeptide characterization and classifications: an analysis using ConoServer. Toxicon (2010) 55:1491-1509

Khan, S. A., Zafar, Y., Briddon, R. W., Malik, K. A. and Mukhtar, Z. Spider venom toxin protects plants from insect attack. Trangenic Research (2006) 15:349-357

Nielsen, H., Engelbrecht, J., Brunak, S. and von Heijne, G. Identification of prokaryotic and eukaryotic signal peptides and prediction of their cleavage sites. Protein Engineering (1997) 10:1-6

Sambrook & Russell, Molecular Cloning: A Laboratory Manual: $3^{rd}$ edition

Sherman et al (1986) Methods in Yeast Genetics, A Laboratory Manual. Cold Spring Harbour, NY.

Southern. Detection of specific sequences among DNA fragments separated by gel electrophoresis. J. Mol. Biol (1975) 98:503-517

Tedford, Sollod, Maggio and King. Australian funnel-web spiders; master insecticide chemists. Toxicon (2004) 43:601-618

Windley, Herzig, Dziemborowicz, Hardy, King and Nicholson. Spider-Venom Peptides as Bioinsecticides. Toxins (2012) 4:191-227

Wong, E. S., Hardy, M. C., Wood, D., Bailey, T. and King, G. F. SVM-based prediction of propeptide cleavage sites in spider toxins identifies toxin innovation in an Australian tarantula. PLoS One (2013) 8(7):e66279

The invention claimed is:

1. A method for increasing the pesticidal activity of a recombinant toxin, the method comprising:

expressing a nucleic acid construct in vitro encoding a recombinant toxin fusion protein comprising the recombinant toxin linked to a carrier protein and a pro-region of a native toxin, the nucleic acid construct comprising:

(i) a nucleic acid sequence encoding the recombinant toxin;

(ii) a nucleic acid sequence encoding the pro-region of a native toxin; and (iii) a nucleic acid sequence encoding the carrier protein selected from snowdrop lectin (GNA), garlic lectin *Allium sativum*, pea lectin *Pisum sativum*(P-lec), peanut lectin *Arachis hypogaea*, or french bean lectin (PHA, phytohaemagglutinin).

2. The method of claim 1, wherein the recombinant toxin is an arthropod toxin.

3. The method of claim 1, wherein the recombinant toxin is ω-ACTX-Hv1a.

4. The method of claim 1, wherein the recombinant toxin is δ-amaurobitoxin-PI1a.

5. The method of claim 1, wherein the pro-region is rich in acidic amino acid residues.

6. The method of claim 1, wherein the pro-region comprises the amino acid sequence EDTRADLQGGEAAEKVFRR (SEQ ID NO: 1).

7. The method of claim 1, wherein the pro-region comprises the amino acid sequence ISYEEGKELFQKER (SEQ ID NO: 2).

8. The method of claim 1, wherein the pro-region alters or improves the folding of the recombinant toxin.

9. The method of claim 1, wherein the carrier protein is snowdrop lectin (GNA).

10. The method of claim 1, wherein the pro-region is a sequence between a signal peptide sequence and a mature protein N-terminus of a native toxin;

optionally wherein the pro-region is identifiable by the steps of:

comparing a sequence for a protein toxin isolated from its source with a sequence predicted by a gene encoding it;

identifying N-terminal sequences not present in the isolated protein toxin sequence;

identifying a signal peptide sequence in the N-terminal sequence not present in the isolated protein toxin sequence; and identifying the pro-region sequence between the signal peptide sequence and the isolated protein toxin sequence N-terminus.

11. A recombinant toxin fusion protein produced by the method of claim 1.

12. A pesticide composition comprising the recombinant toxin fusion protein produced by the method of claim 1.

13. The pesticide composition of claim 12, wherein the composition comprises the recombinant toxin fusion protein in an amount of between 0.001% and 99% by weight; between 0.5% and 98% by weight; or between 1.0% and 95% by weight.

14. A process for preparing a pesticide composition comprising an admixture of a pesticidal effective amount of the recombinant toxin fusion protein produced by the method of claim 1, with one or more suitable carriers, diluents, adjuvants, preservatives, dispersants, solvents, or emulsifying agents.

15. A molluscicide bait composition comprising the recombinant toxin fusion protein produced by the method of claim 1.

16. A method for treating a pest infection of a plant comprising applying a quantity of the recombinant toxin fusion protein produced by the method of claim 1 to the plant or its locus of growth.

17. A nucleic acid construct encoding the recombinant toxin fusion protein of claim 1.

18. The nucleic acid construct of claim 17, wherein the toxin gene sequence is adjacent to the pro-region sequence.

19. The nucleic acid construct of claim 17, wherein the nucleic acid construct is an expression construct.

20. The nucleic acid construct of claim 17, further comprising a sequence encoding an affinity tag.

21. A transgenic plant or progeny thereof having increased biological activity resulting from the expression of the recombinant toxin fusion protein encoded by the nucleic acid construct of claim 17.

* * * * *

SEQUENCE LISTING

```
<160> NUMBER OF SEQ ID NOS: 19

<210> SEQ ID NO 1
<211> LENGTH: 19
<212> TYPE: PRT
<213> ORGANISM: Hadronyche versuta

<400> SEQUENCE: 1

Glu Asp Thr Arg Ala Asp Leu Gln Gly Gly Glu Ala Ala Glu Lys Val
1               5                   10                  15

Phe Arg Arg


<210> SEQ ID NO 2
<211> LENGTH: 14
<212> TYPE: PRT
<213> ORGANISM: Agelena orientalis

<400> SEQUENCE: 2

Ile Ser Tyr Glu Glu Gly Lys Glu Leu Phe Gln Lys Glu Arg
1               5                   10


<210> SEQ ID NO 3
<211> LENGTH: 25
<212> TYPE: DNA
<213> ORGANISM: Unknown
<220> FEATURE:
<223> OTHER INFORMATION: PCR primer

<400> SEQUENCE: 3

tactgcagca gaagatacta gagct                                            25


<210> SEQ ID NO 4
<211> LENGTH: 23
<212> TYPE: DNA
<213> ORGANISM: Unknown
<220> FEATURE:
<223> OTHER INFORMATION: PCR primer

<400> SEQUENCE: 4

attctagaat cacatctctt aac                                              23


<210> SEQ ID NO 5
<211> LENGTH: 25
<212> TYPE: DNA
<213> ORGANISM: Unknown
<220> FEATURE:
<223> OTHER INFORMATION: PCR primer

<400> SEQUENCE: 5

atgcggccgc atcacatctc ttaac                                            25


<210> SEQ ID NO 6
<211> LENGTH: 37
<212> TYPE: PRT
<213> ORGANISM: Hadronyche versuta
```

<400> SEQUENCE: 6

```
Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35
```

<210> SEQ ID NO 7
<211> LENGTH: 138
<212> TYPE: PRT
<213> ORGANISM: Hadronyche versuta

<400> SEQUENCE: 7

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Trp Ser His Pro Gln Phe
                85                  90                  95

Glu Lys Gly Leu Gln Ser Pro Thr Cys Ile Pro Ser Gly Gln Pro Cys
            100                 105                 110

Pro Tyr Asn Glu Asn Cys Cys Ser Gln Ser Cys Thr Phe Lys Glu Asn
        115                 120                 125

Glu Asn Gly Asn Thr Val Lys Arg Cys Asp
    130                 135
```

<210> SEQ ID NO 8
<211> LENGTH: 170
<212> TYPE: PRT
<213> ORGANISM: Hadronyche versuta

<400> SEQUENCE: 8

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ala Glu Asp Thr Arg Ala
                85                  90                  95

Asp Leu Gln Gly Gly Glu Ala Ala Glu Lys Val Phe Arg Arg Ser Pro
            100                 105                 110

Thr Cys Ile Pro Ser Gly Gln Pro Cys Pro Tyr Asn Glu Asn Cys Cys
        115                 120                 125

Ser Gln Ser Cys Thr Phe Lys Glu Asn Glu Asn Gly Asn Thr Val Lys
```

```
    130                 135                 140

Arg Cys Asp Ala Leu Glu Gln Lys Leu Ile Ser Glu Glu Asp Leu Asn
145                 150                 155                 160

Ser Ala Val Asp His His His His His His
                165                 170


<210> SEQ ID NO 9
<211> LENGTH: 238
<212> TYPE: PRT
<213> ORGANISM: Hadronyche versuta

<400> SEQUENCE: 9

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ala Ser Pro Thr Cys Ile
                85                  90                  95

Pro Ser Gly Gln Pro Cys Pro Tyr Asn Glu Asn Cys Cys Ser Gln Ser
            100                 105                 110

Cys Thr Phe Lys Glu Asn Glu Asn Gly Asn Thr Val Lys Arg Cys Asp
        115                 120                 125

Ala Ala Ala Asp Asn Ile Leu Tyr Ser Gly Glu Thr Leu Ser Thr Gly
    130                 135                 140

Glu Phe Leu Asn Tyr Gly Ser Phe Val Phe Ile Met Gln Glu Asp Cys
145                 150                 155                 160

Asn Leu Val Leu Tyr Asp Val Asp Lys Pro Ile Trp Ala Thr Asn Thr
                165                 170                 175

Gly Gly Leu Ser Arg Ser Cys Phe Leu Ser Met Gln Thr Asp Gly Asn
            180                 185                 190

Leu Val Val Tyr Asn Pro Ser Asn Lys Pro Ile Trp Ala Ser Asn Thr
        195                 200                 205

Gly Gly Gln Asn Gly Asn Tyr Val Cys Ile Leu Gln Lys Asp Arg Asn
    210                 215                 220

Val Val Ile Tyr Gly Thr Asp Arg Trp Ala Thr Gly Val Asp
225                 230                 235


<210> SEQ ID NO 10
<211> LENGTH: 263
<212> TYPE: PRT
<213> ORGANISM: Hadronyche versuta

<400> SEQUENCE: 10

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
```

```
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ala Glu Asp Thr Arg Ala
                85                  90                  95

Asp Leu Gln Gly Gly Glu Ala Ala Glu Lys Val Phe Arg Arg Ser Pro
            100                 105                 110

Thr Cys Ile Pro Ser Gly Gln Pro Cys Pro Tyr Asn Glu Asn Cys Cys
        115                 120                 125

Ser Gln Ser Cys Thr Phe Lys Glu Asn Glu Asn Gly Asn Thr Val Lys
    130                 135                 140

Arg Cys Asp Ala Ala Ala Asp Asn Ile Leu Tyr Ser Gly Glu Thr Leu
145                 150                 155                 160

Ser Thr Gly Glu Phe Leu Asn Tyr Gly Ser Phe Val Phe Ile Met Gln
                165                 170                 175

Glu Asp Cys Asn Leu Val Leu Tyr Asp Val Asp Lys Pro Ile Trp Ala
            180                 185                 190

Thr Asn Thr Gly Gly Leu Ser Arg Ser Cys Phe Leu Ser Met Gln Thr
        195                 200                 205

Asp Gly Asn Leu Val Val Tyr Asn Pro Ser Asn Lys Pro Ile Trp Ala
    210                 215                 220

Ser Asn Thr Gly Gly Gln Asn Gly Asn Tyr Val Cys Ile Leu Gln Lys
225                 230                 235                 240

Asp Arg Asn Val Val Ile Tyr Gly Thr Asp Arg Trp Ala Thr Gly Val
                245                 250                 255

Asp His His His His His His
            260


<210> SEQ ID NO 11
<211> LENGTH: 37
<212> TYPE: PRT
<213> ORGANISM: Pireneitega luctuosa

<400> SEQUENCE: 11

Gly Cys Leu Gly Glu Gly Glu Lys Cys Ala Asp Trp Ser Gly Pro Ser
1               5                   10                  15

Cys Cys Asp Gly Phe Tyr Cys Ser Cys Arg Ser Met Pro Tyr Cys Arg
            20                  25                  30

Cys Arg Asn Asn Ser
        35


<210> SEQ ID NO 12
<211> LENGTH: 151
<212> TYPE: PRT
<213> ORGANISM: Pireneitega luctuosa

<400> SEQUENCE: 12

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
```

-continued

```
65                  70                  75                  80

Ser Leu Glu Lys Arg Glu Ala Glu Ala Ala Ala Gly Cys Leu Gly Glu
                85                  90                  95

Gly Glu Lys Cys Ala Asp Trp Ser Gly Pro Ser Cys Cys Asp Gly Phe
            100                 105                 110

Tyr Cys Ser Cys Arg Ser Met Pro Tyr Cys Arg Cys Arg Asn Asn Ser
        115                 120                 125

Ala Leu Glu Gln Lys Leu Ile Ser Glu Glu Asp Leu Asn Ser Ala Val
    130                 135                 140

Asp His His His His His His
145                 150


<210> SEQ ID NO 13
<211> LENGTH: 164
<212> TYPE: PRT
<213> ORGANISM: Pireneitega luctuosa

<400> SEQUENCE: 13

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ala Ile Ser Tyr Glu Glu
                85                  90                  95

Gly Lys Glu Leu Phe Gln Lys Glu Arg Gly Cys Leu Gly Glu Gly Glu
            100                 105                 110

Lys Cys Ala Asp Trp Ser Gly Pro Ser Cys Cys Asp Gly Tyr Cys Ser
        115                 120                 125

Cys Arg Ser Met Pro Tyr Cys Arg Cys Arg Asn Asn Ser Ala Leu Glu
    130                 135                 140

Gln Lys Leu Ile Ser Glu Glu Asp Leu Asn Ser Ala Val Asp His His
145                 150                 155                 160

His His His His


<210> SEQ ID NO 14
<211> LENGTH: 244
<212> TYPE: PRT
<213> ORGANISM: Pireneitega luctuosa

<400> SEQUENCE: 14

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80
```

-continued

```
Ser Leu Glu Lys Arg Glu Ala Glu Ala Ala Ala Gly Cys Leu Gly Glu
                85                  90                  95

Gly Glu Lys Cys Ala Asp Trp Ser Gly Pro Ser Cys Cys Asp Gly Phe
            100                 105                 110

Tyr Cys Ser Cys Arg Ser Met Pro Tyr Cys Arg Cys Arg Asn Asn Ser
        115                 120                 125

Ala Ala Ala Asp Asn Ile Leu Tyr Ser Gly Glu Thr Leu Ser Thr Gly
    130                 135                 140

Glu Phe Leu Asn Tyr Gly Ser Phe Val Phe Ile Met Gln Glu Asp Cys
145                 150                 155                 160

Asn Leu Val Leu Tyr Asp Val Asp Lys Pro Ile Trp Ala Thr Asn Thr
                165                 170                 175

Gly Gly Leu Ser Arg Ser Cys Phe Leu Ser Met Gln Thr Asp Gly Asn
            180                 185                 190

Leu Val Val Tyr Asn Pro Ser Asn Lys Pro Ile Trp Ala Ser Asn Thr
        195                 200                 205

Gly Gly Gln Asn Gly Asn Tyr Val Cys Ile Leu Gln Lys Asp Arg Asn
    210                 215                 220

Val Val Ile Tyr Gly Thr Asp Arg Trp Ala Thr Gly Val Asp His His
225                 230                 235                 240

His His His His


<210> SEQ ID NO 15
<211> LENGTH: 256
<212> TYPE: PRT
<213> ORGANISM: Pireneitega luctuosa

<400> SEQUENCE: 15

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ala Ile Ser Tyr Glu Glu
                85                  90                  95

Gly Lys Glu Leu Phe Gln Lys Glu Arg Gly Cys Leu Gly Glu Gly Glu
            100                 105                 110

Lys Cys Ala Asp Trp Ser Gly Pro Ser Cys Cys Asp Gly Cys Ser Cys
        115                 120                 125

Arg Ser Met Pro Tyr Cys Arg Cys Arg Asn Asn Ser Ala Ala Ala Asp
    130                 135                 140

Asn Ile Leu Tyr Ser Gly Glu Thr Leu Ser Thr Gly Glu Phe Leu Asn
145                 150                 155                 160

Tyr Gly Ser Phe Val Phe Ile Met Gln Glu Asp Cys Asn Leu Val Leu
                165                 170                 175

Tyr Asp Val Asp Lys Pro Ile Trp Ala Thr Asn Thr Gly Gly Leu Ser
            180                 185                 190

Arg Ser Cys Phe Leu Ser Met Gln Thr Asp Gly Asn Leu Val Val Tyr
        195                 200                 205
```

```
Asn Pro Ser Asn Lys Pro Ile Trp Ala Ser Asn Thr Gly Gly Gln Asn
    210                 215                 220

Gly Asn Tyr Val Cys Ile Leu Gln Lys Asp Arg Asn Val Val Ile Tyr
225                 230                 235                 240

Gly Thr Asp Arg Trp Ala Thr Gly Val Asp His His His His His His
                245                 250                 255


<210> SEQ ID NO 16
<211> LENGTH: 262
<212> TYPE: PRT
<213> ORGANISM: Pireneitega luctuosa

<400> SEQUENCE: 16

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ala Glu Asp Thr Arg Ala
                85                  90                  95

Asp Leu Gln Gly Gly Glu Ala Ala Glu Lys Val Phe Arg Arg Gly Cys
            100                 105                 110

Leu Gly Glu Gly Glu Lys Cys Ala Asp Trp Ser Gly Pro Cys Cys Asp
        115                 120                 125

Gly Phe Tyr Cys Ser Cys Arg Ser Met Pro Tyr Cys Arg Cys Arg Asn
    130                 135                 140

Asn Ser Ala Ala Ala Asp Asn Ile Leu Tyr Ser Gly Glu Thr Leu Ser
145                 150                 155                 160

Thr Gly Glu Phe Leu Asn Tyr Gly Ser Phe Val Phe Ile Met Gln Glu
                165                 170                 175

Asp Cys Asn Leu Val Leu Tyr Asp Val Asp Lys Pro Ile Trp Ala Thr
            180                 185                 190

Asn Thr Gly Gly Leu Ser Arg Ser Cys Phe Leu Ser Met Gln Thr Asp
        195                 200                 205

Gly Asn Leu Val Val Tyr Asn Pro Ser Asn Lys Pro Ile Trp Ala Ser
    210                 215                 220

Asn Thr Gly Gly Gln Asn Gly Asn Tyr Val Cys Ile Leu Gln Lys Asp
225                 230                 235                 240

Arg Asn Val Val Ile Tyr Gly Thr Asp Arg Trp Ala Thr Gly Val Asp
                245                 250                 255

His His His His His His
            260


<210> SEQ ID NO 17
<211> LENGTH: 8
<212> TYPE: PRT
<213> ORGANISM: Unknown
<220> FEATURE:
<223> OTHER INFORMATION: Artificial

<400> SEQUENCE: 17
```

-continued

```
Trp Ser His Pro Gln Phe Glu Lys
1               5


<210> SEQ ID NO 18
<211> LENGTH: 5
<212> TYPE: PRT
<213> ORGANISM: Unknown
<220> FEATURE:
<223> OTHER INFORMATION: Single band sequence

<400> SEQUENCE: 18

Glu Ala Ala Ala Gly
1               5


<210> SEQ ID NO 19
<211> LENGTH: 56
<212> TYPE: PRT
<213> ORGANISM: Hadronyche versuta

<400> SEQUENCE: 19

Glu Asp Thr Arg Ala Asp Leu Gln Gly Gly Glu Ala Ala Glu Lys Val
1               5                   10                  15

Phe Arg Arg Ser Pro Thr Cys Ile Pro Ser Gly Gln Pro Cys Pro Tyr
            20                  25                  30

Asn Glu Asn Cys Cys Ser Gln Ser Cys Thr Phe Lys Glu Asn Glu Asn
        35                  40                  45

Gly Asn Thr Val Lys Arg Cys Asp
    50                  55
```